(12) United States Patent
Chakraborty et al.

(10) Patent No.: US 9,790,529 B2
(45) Date of Patent: *Oct. 17, 2017

(54) PSYCHROPHILIC ENZYMES COMPOSITIONS AND METHODS FOR MAKING AND USING SAME

(71) Applicant: University of Calcutta, Kolkataa, West Bengal (IN)

(72) Inventors: Krishanu Chakraborty, Kolkata (IN); Arka Mukhopadhyay, Howrah (IN); Nalok Dutta, Kolkata (IN); Anjan Kr. Dasgupta, Kolkata (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 71 days.

This patent is subject to a terminal disclaimer.

(21) Appl. No.: 14/455,699

(22) Filed: Aug. 8, 2014

(65) Prior Publication Data
US 2015/0044731 A1 Feb. 12, 2015

(30) Foreign Application Priority Data
Aug. 9, 2013 (IN) .............................. 944/KOL/2013

(51) Int. Cl.
| | |
|---|---|
| C12P 13/00 | (2006.01) |
| C12P 19/02 | (2006.01) |
| C12P 19/14 | (2006.01) |
| C12N 9/96 | (2006.01) |
| C12N 9/02 | (2006.01) |
| C12N 9/42 | (2006.01) |
| C12N 9/24 | (2006.01) |
| C12N 9/88 | (2006.01) |
| C12P 21/00 | (2006.01) |
| C12P 21/06 | (2006.01) |
| C12P 13/04 | (2006.01) |

(52) U.S. Cl.
CPC ............ *C12P 19/02* (2013.01); *C12N 9/0061* (2013.01); *C12N 9/248* (2013.01); *C12N 9/2437* (2013.01); *C12N 9/88* (2013.01); *C12N 9/96* (2013.01); *C12P 13/04* (2013.01); *C12P 19/14* (2013.01); *C12P 21/00* (2013.01); *C12P 21/06* (2013.01); *C12Y 110/03002* (2013.01); *C12Y 302/01* (2013.01); *C12Y 302/01015* (2013.01); *C12Y 302/01067* (2013.01); *C12Y 402/02002* (2013.01)

(58) Field of Classification Search
None
See application file for complete search history.

(56) References Cited

U.S. PATENT DOCUMENTS

| | | | |
|---|---|---|---|
| 5,795,855 A | 8/1998 | Schneider et al. | |
| 8,097,441 B2* | 1/2012 | Peng | C12N 11/14 435/165 |
| 9,227,099 B2* | 1/2016 | Cabrera | A62D 3/02 |
| 9,322,012 B2* | 4/2016 | Dasgupta | C12N 11/04 |
| 2001/0037532 A1 | 11/2001 | Barfoed et al. | |
| 2005/0089980 A1 | 4/2005 | Kruus et al. | |
| 2006/0147512 A1 | 7/2006 | Sabin | |

FOREIGN PATENT DOCUMENTS

| | | |
|---|---|---|
| GB | 2304107 A | 3/1997 |
| MX | PA05002751 | 6/2005 |
| WO | WO 2004023879 | 3/2004 |
| WO | WO 2006056838 | 6/2006 |
| WO | WO-2013/114149 A1 | 8/2013 |

OTHER PUBLICATIONS

Mukhopadhyay et al., "Thermostability, pH stability and dye degrading activity of a bacterial laccase are enhanced in the presence of Cu2O nanoparticles", Bioresource Technology 127: 25-36 (2013).*

Brondani et al.,"PEI-coated gold nanoparticles decorated with laccase: A platform for direct electrochemistry of enzymes and biosensing applications", Biosensors and Bioelectronics 42: 242-247 (2013).*

Abadulla, E., et al., "Decolorization and detoxification of textile dyes with a laccase from Trametes hirsute," Applied and Environmental Microbiology, vol. 66, No. 8, pp. 3357-3362 (Aug. 2000).

Akhtar, M., et al., "Fungal delignification and biomechanical pulping of wood," In Advances in biochemical engineering and biotechnology, Berlin: Springer-Verlag, vol. 57, pp. 159-195 (1997).

Baek et al., "Microbial toxicity of metal oxide nanoparticles (CuO, NiO, ZnO, and $Sb_2O_3$) to *Escherichia coli*, Bacillus subtilis, and *Streptococcus aureus*," Science of the Total Environment, 2011, 409: 1603-1608.

Banat, I. M., "Microbial Decolorization of Textile-Dye-Containing Effluents: A Review," Bioresource Technology, vol. 58, pp. 217-227 (1996).

Barner, B. A., "Catechol," Published Online Sep. 15, 2008, Encyclopedia of Reagents for Organic Synthesis, 3rd Ed., L. Paquette, J. Wiley & Sons, New York, pp. 2116-2119.

Behrendt, C.J., "Biomechanical pulping with Phlebiopsis gigantea reduced energy consumption and increased paper strength," Tappi journal, vol. 83, No. 9, pp. 65 (Sep. 2000).

Blánquez, P., et al., "Mechanism of textile metal dye biotransformation by Trametes versicolor," Water Research, vol. 38, No. 8, pp. 2166-2172 (Apr. 2004).

Bollag, J.M., et al., "Laccase-mediated detoxification of phenolic compounds," Appl. Environ. Microbiol., vol. 54, No. 12, pp. 3086-3091 (Dec. 1998).

Chawla, S., et al., "Fabrication of polyphenol biosensor based on laccase immobilized on copper nanoparticles/chitosan/multiwalled carbon nanotubes/polyaniline-modified gold electrode," Journal of Biotechnol., vol. 156, No. 1, pp. 39-45 (Oct. 20, 2011).

(Continued)

*Primary Examiner* — Anand Desai
(74) *Attorney, Agent, or Firm* — Maschoff Brennan

(57) ABSTRACT

Enzyme compositions with enhanced enzyme activity and/or thermophilic and psychrophilic stability are described. Additionally, methods and kits for making and using the enzyme compositions are provided.

23 Claims, 22 Drawing Sheets

(56) References Cited

OTHER PUBLICATIONS

Cho, N.S., et al., "Removal of chlorophenols by fungal laccase in the presence of aromatic alcohols," Journal of the Faculty of Agriculture Kyushu University, vol. 52, No. 1, pp. 23-27 (2007).

Couto, S. R., and Herrera, J. L. T., "Industrial and biotechnological applications of laccases: A review," Biotechnology Advances, vol. 24, No. 5, pp. 500-513 (Sep.-Oct. 2006).

Couto, S. R., and Herrera, J. L. T., "Lacasses in the textile industry," Biotechnology and Molecular Biology Review, vol. 1, No. 4, pp. 115-120 (Dec. 2006).

Couto, S. R., et al., "Production of Laccase by Trametes Hirsuta Grown in an Immersion Bioreactor and Its Application in the Decolorization of Dyes from a Leather Factory," Engineering in Life Sciences, vol. 4, Issue 3, pp. 233-238 (Jun. 2004).

Fiege, H., et al., "Phenol Derivatives," in Ullmann's Encyclopedia of Industrial Chemistry, Wiley-VCH, 62 pages (Jun. 15, 2000).

Gajjar et al., "Antimicrobial activities of commercial nanoparticles against an environmental soil microbe, Pseudomonas putida KT2440," Journal of Biological Engineering, Jun. 26, 2009, 3(9): 1-13.

Gianfreda, L. et al., "Laccases: a useful group of oxidoreductive enzymes," vol. 3, No. 1, pp. 1-26 (1999).

Goor, G., "Hydrogen Peroxide," in Ullmann's Encyclopedia of Industrial Chemistry, Wiley-VCH, 36 pages (Apr. 15, 2007).

Hedin, P. A., et al., "Evaluation of flavonoids in *Gossypium arboreum* (L.) cottons as potential source of resistance to tobacco budworm," J. Chem. Ecol., vol. 18, No. 2, pp. 105-114 (1992).

Howard, R.S., et al., "Lignocellulose biotechnology: issues of bioconversion and enzyme production," African Journal of Biotechnology, vol. 2, No. 12, pp. 602-619 (Dec. 2003).

International Search Report and Written Opinion for International Patent Application No. PCT/IB2013/055396, mailed Jan. 10, 2014.

Kandelbauer et al., "Study of Dye Decolorization in an Immobilized Laccase Enzyme-Reactor Using Online Spectroscopy," Biotechnology and Bioengineering, 2004, 87(4): 552-563.

Leatham, G. F., et al., "Biomechanical pulping of aspen chips: energy savings resulting from different fungal treatments," Tappi Journal, vol. 73, No. 5, pp. 197-200 (May 1990).

Liao, C.-H., et al., "Biochemical characterization of pectate lyases produced by fluorescent Pseudomonads associated with spoilage of fresh fruits and vegetables," Journal of Applied Microbiology, vol. 83, Issue 1, pp. 10-16 (Nov. 25, 2003).

Ortega, N., et al., "Kinetic behaviour and thermal inactivation of pectinlyase used in food processing," International Journal of Food Science & Technology, vol. 39, No. 6, pp. 631-639 (Jun. 2004).

Pearce, C. I., et al., "The removal of colour from textile wastewater using whole bacterial cells: a review," Dyes Pigments, vol. 58, Issue 3, pp. 179-196 (Sep. 2003).

Pereira, L., et al., "Environmentally friendly bleaching of cotton using laccases," Environ. Chem. Lett., vol. 3, pp. 66-69 (2005).

Pierce, J., "Colour in textile effluents—the origins of the problem," Journal of the Society of Dyers and Colourists, vol. 110, Issue 4, pp. 131-134 (Apr. 1994).

Pradhan et al., "Copper oxide nanoparticles induce oxidative stress, DNA strand breaks and laccase activity in aquatic fungi," SETAC meeting abstract, 2011, 1 page.

Raghukumar, C., et al., "Treatment of colored effluents with lignin-degrading enzymes: An emerging role of marine-derived fungi," Critical Reviews in Microbiology, vol. 34, No. 3-4, pp. 189-206 (2008).

Scott, G.M., et al., "Recent developments in biopulping technology at Madison, WI," Progress in Biotechnology, vol. 21, pp. 61-71 (2002).

Selvam, K., et al., "Pretreatment of wood chips and pulps with Fomes lividus and Trametes versicolor to reduce chemical consumption in paper industries," Asian Jr. of Microbiol. Biotechnol. Environ. Sci., vol. 8, No. 4, pp. 771-776 (2006).

Shraddha et al., "Laccase: Microbial Sources, Production, Purification, and Potential Biotechnological Applications," Enzyme Research, 2011, pp. 1-11.

Solbak, A. I., et al., "Discovery of Pectin-Degrading Enzymes and Directed Evolution of a Novel Pectate Lyase for Processing Cotton Fabric," Journal of Biological Chemistry, vol. 280, No. 10, pp. 9431-9438 (Mar. 11, 2005).

Taherzadeh, M.J., and Karimi, K., "Pretreatment of Lignocellulosic Wastes to Improve Ethanol and Biogas Production: A Review," Int. J. Mol. Sci., vol. 9, No. 9, pp. 1621-1651 (Sep. 2008).

Tzanov, T., et al., "Bio-preparation of cotton fabrics, Enzyme and Microbial Technology," vol. 29, Issues 6-7, pp. 357-362 (Oct. 4, 2001).

Van Beek, T.A., et al., "Fungal bio-treatment of spruce wood with Trametes versicolor for pitch control: Influence on extractive contents, pulping process parameters, paper quality and effluent toxicity," Bioresour Technology, vol. 98, pp. 302-311 (2007).

Ohgiya, S., "Biotechnology of enzymes from cold-adapted microorganisms," In: Margesin, R. and Schinner F. (Eds.) Spriger, 17-34 (1999).

Sproessler, B.G., "Milling and baking," In Enzymes in Food Processing (Nagodawithana, T. and Reed, G., eds), pp. 293013320, (1993).

Tolan, J. S., and Foody, B., "Cellulase from submerged fermentation," Advanced Biochemical Engineering and Biotechnology, vol. 65, pp. 4101367 (1999).

Beg, Q. K. et al., "Microbial xylanases and their industrial applications: a review," Appl Microbiol Biotechnol, vol. 56, No. 3-4, pp. 326-338 (2001).

Bhandari, N., "Kinetic studies of corn stover saccharification using sulphuric acid," Biotech. Bioeng, vol. 26, pp. 320-327 (1984).

Carrion, J., "Hemicellulose removal from corn stalk thermochemical treatment in aqueous medium," Lisbon, Portugal, 2.45-2.49 (1989).

Cavicchioli, R. et al., "Low-temperature extremophiles and their applications," Current Opinion in Biotechnology, vol. 13, pp. 253-261 (2002).

Collins, T. et al., "Use of glycoside family 8 xylanases in baking," J Cereal Sci, vol. 43, pp. 79-84 (2006).

Collins, T., et al., "Activity, stability and flexibility in glycosidases adapted to extreme thermal environments," J. Mol. Biol. vol. 328, pp. 419-428 (2003).

Couto, S. R. and Toca-Herrera, J. L., "Lacasses in the textile industry," Biotechnology and Molecular Biology Review, vol. 1, No. 4, pp. 115-120 (2006).

Couto, S. R. et al., "Industrial and biotechnological applications of laccases," A review; Biotechnology Advances, vol. 24, pp. 500-513 (2006).

Curreli, N., "Mild alkaline/ oxidative pretreatment of wheat straw," Process Biochemistry, vol. 32, pp. 665-670 (1997).

D'Amico, S. et al., "Activity—stability relationships in extremophilic enzymes," J. Biol. Chem., vol. 278, No. 10, pp. 7891-7896 (2003).

Feller, G. and Gerday, C., "Psychrophilic Enzymes: Hot Topics in Cold Adaptation," Nature review, microbiology, vol. 1, pp. 200-208 (2003).

Garrote, G. et al., "Autohydrolysis of corncob:study of non-isothermal operation for xylooligosaccharide production," Journal of Food Engineering, vol. 52, No. 3, pp. 211-218 (2001).

Gaspar, M. et al., "Fractionation and utilization of corn fibre carbohydrates," Process Biochemistry, vol. 40, No. 3-4, 1183-1188 (2005).

Georlette, D. et al., "Structural and functional adaptations to extreme temperatures in psychrophilic, mesophilic and thermophilic DNA ligases," J. Biol. Chem., vol. 278, pp. 37015-37023 (2003).

Gerday, C. et al., "Cold—adapted enzymes: from fundamentals to biotechnology," Trends Biotechnol., vol. 18, pp. 103-107 (2000).

Ho, N.W.Y., et al., "Genetically engineered *Saccharomyces* yeast capable of effective cofermentation of glucose and xylose," Applied and Environmental Microbiology, vol. 64, pp. 1852-1859 (1998).

Howard, R. L. et al., "Lignocellulose biotechnology: issues of bioconversion and enzyme production," African Journal of Biotechnology, vol. 2, No. 12, pp. 602-619 (2003).

(56) References Cited

OTHER PUBLICATIONS

Huston, A. L., "Biotechnological Aspects of Cold-Adapted Enzymes," Psychrophiles: from Biodiversity to Biotechnology, pp. 347-363 (2008).
Kashyap, D. R. et al., "Applications of pectinases in the commercial sector: a review," Bioresource Technology, vol. 77, pp. 215-227 (2001).
Kuhad, R. C. et al., "Microbial Cellulases and Their Industrial Applications," Enzyme Research, vol. 2011, Article ID 280696, pp. 10 (2011).
Lamptey, J., "Enhanced enzymatic hydrolysis of lignocellulosic biomass pretreatment by low-pressure steam autohydrolysis," Biotech. Lett., vol. 7, No. 7, pp. 531-534 (1985).
Lee, Y.Y. et al., "Kinetic and Modeling Investigation on Dilute-Acid Pretreatment of Hardwood, Hardwood Bark, and Corn Cobs/Stover Mixture Feedstocks," Annual Report for NREL Subcontract XAW-3-13441-01, pp. 114 (1995).
Lloyd, T., and Wyman, C.E., "Application of a depolymerization model for predicting thermochemical hydrolysis of hemicellulose," Applied Biochemistry and Biotechnology, vol. 105, pp. 53-67 (2003).
Lynd, L.R. et al., "Likely features and costs of mature biomass ethanol technology," Appl. Biochem. Biotechnol., vol. 57/58, pp. 741-761 (1996).
Margesin, R. and Schinner, F., "Biodegradation of organic pollutants at low temperatures," In Biotechnological Applications of Cold Adapted Organisms, pp. 271-289 (1999).
Moniruzzaman, M., et al., "Fermentation of corn fibre sugars by an engineered xylose utilizing *Saccharomyces* yeast strain," World Journal of Microbiology and Biotechnology, vol. 13, pp. 341-346 (1997).
Morita, R., "Psychrophilic bacteria," Bacteriol Rev, vol. 39, No. 2, pp. 144-169 (1975).
Mukhopadhyay, A. et al., "Thermostability, pH stability and dye degrading activity of a bacterial laccase are enhanced in the presence of Cu2O nanoparticles," Bioresource Technology, vol. 127, pp. 25-36 (2013).
Mukhopadhyay, A. et al., "Improvement of thermostability and activity of pectate lyase in the presence of hydroxyapatite nanoparticles," Bioresource Technology, vol. 116, pp. 348-354 (2012).
Narinx, E. et al., "Subtilisin from psychrophilic antarctic bacteria: characterization and sitedirected mutagenesis of residues possibly involved in the adaptation to cold," Protein Eng., vol. 10, No. 11, pp. 1271-1279 (1997).

O'Neill, C. et al., "Colour in textile effluents—sources, measurement, discharge consents and simulation: a review," J Chem Technol Biotechnol, vol. 74, pp. 1009-1018 (1999).
Russell, N. J., "Molecular adaptations in psychrophilic bacteria: potential for biotechnological applications," Adv. Biochem. Eng. Biotechnol., vol. 61, pp. 1-21 (1998).
Sabri, A. et al., "Influence of moderate temperatures on myristoyl-CoA metabolism and acyl-CoA thioesterase activity in the psychrophilic antarctic yeast Rhodotorula aurantiaca," J. Biol. Chem., vol. 276, No. 16, pp. 12691-12696 (2001).
Sadasivam, S. and Manikam, A., "Biochemical Methods for agricultural sciences," New Age International publishing house, p. 41-42 (1991).
Schultz, T.P. et al., "Steam explosion of mixed hardwood chips, rice hulls, corn stalk, and sugar cane bagasse," J. Agric. Food Chem., vol. 32, No. 5, pp. 1166-1172, (1984).
Sun, Y., and Cheng, J.Y., "Hydrolysis of lignocellulosic materials for ethanol production: a review," Bioresource Technology, vol. 83, pp. 1-11 (2002).
Taherzadeh, M. and Karimi, K., "Pretreatment of Lignocellulosic Wastes to Improve Ethanol and Biogas Production: A Review," Int. J. Mol. Sci., vol. 9, pp. 1621-1651 (2008).
Timmis, K.N. and Pieper, D.H., "Bacteria designed for bioremediation," Trends Biotechnol., vol. 17, No. 5, pp. 201-204 (1999).
Torget, R., et al., "Dilute-acid pretreatment of corn residues and short rotation woody crops," Appl. Biochem. Biotechnol., vol. 28/29, pp. 75-86 (1991).
Tucker, M.P. et al., "Effects of temperature and moisture on dilute-acid steam explosion pretreatment of corn stover and cellulase enzyme digestibility," Appl. Biochem. Biotechnol., vol. 105, No. (1-3), pp. 165-178 (2003).
Wyman, C.E., "Potential synergies and challenges in refining cellulosic biomass to fuels, chemicals, and power," Biotechnol Prog, vol. 19, pp. 254-262 (2003).
"Psychrophilic Enzyme and Its Industrial Application," 2001, pp. 248-249. (3 pages—English abstract included).
Zhang et al., "Mechanism and applications of the cold-adapted microbes," Acta Ecologica Sinica, Aug. 2008, 28(8): 3921-3926. (7 pages—English abstract included).
Villalonga, R., et al.,"Supramolecular assembly of β-cyclodextrin-moditied gold nanoparticles and Cu, Zn-superoxide dismutase on catalase", Journal of Molecular Catalysis B: Enzymatic, vol. 35, Issue 4-6, pp. 79-85 (Sep. 1, 2005).

\* cited by examiner

A.

B.

C.

D.

A.

B.

C.

D.

E.

F.

G.

H.

A.

B.

C.

D.

E.

F.

G.

H.

A.

B.

C.

D.

A.

B.

A.

B.

A.

B.

A.

B.

A.

B.

A.

B.

PSYCHROPHILIC ENZYMES COMPOSITIONS AND METHODS FOR MAKING AND USING SAME

CROSS-REFERENCE TO RELATED APPLICATION

The present application claims priority to Indian Patent Application No. 944/KOL/2013 filed on Aug. 9, 2013, the content of which is incorporated herein by reference in its entirety.

FIELD

The present technology relates to, among other things, enzyme compositions with enhanced enzyme activity that have industrial applications.

BACKGROUND

The microorganisms that have colonized in cold environments are referred to as psychrophiles. Cold-adapted enzymes are enzymes which have high activity at low temperatures. Typically, the specific activity of cold-adapted enzymes is higher than that of their mesophilic counterparts at low temperatures.

Cold-adapted enzymes offer economic benefits through energy savings: they negate the requirement for expensive heating steps, function in cold environments and during the winter season, provide increased reaction yields, accommodate a high level of stereo-specificity, minimize undesirable chemical reactions that can occur at higher temperatures and exhibit thermal lability for rapidly and easily inactivating the enzyme when required.

SUMMARY

In some aspects, the present technology provides a composition having at least one nanoparticle and at least one psychrophilic enzyme. In some embodiments, the psychrophilic enzyme is in contact with, but is not linked to, the nanoparticle. In some embodiments, the nanoparticle treated psychrophilic enzyme has an enhanced activity compared to a control psychrophilic enzyme. In some embodiments, the composition includes cell free extract from bacteria and at least one nanoparticle, wherein enzymes in the cell free extract have an enhanced activity compared to the control enzymes. In some embodiments, the cell extract is from a psychrophilic bacteria, a mesophilic bacteria, or a combination thereof.

In some aspects, the present technology relates to methods of making an enzyme composition. In some embodiments, the methods include: contacting at least one nanoparticle and at least one psychrophilic enzyme, wherein the psychrophilic enzyme is contacted with the nanoparticle, but is not linked to the nanoparticle.

In one aspect of the present technology relates to a kit including: a plurality of nanoparticles and at least one psychrophilic enzyme. In some embodiments, the kit also includes instructions for combining the psychrophilic enzyme and the nanoparticles to form an enzyme composition.

In one aspect of the present technology relates to composition that includes a plurality of live cells, wherein the live cells are bacterial; and at least one nanoparticle; wherein enzymes in the live cells have an enhanced enzyme activity compared control enzymes. In some embodiments, the live cells include psychrophilic bacteria cells, mesophilic bacteria cells, or a combination thereof.

DETAILED DESCRIPTION

Figure 1:
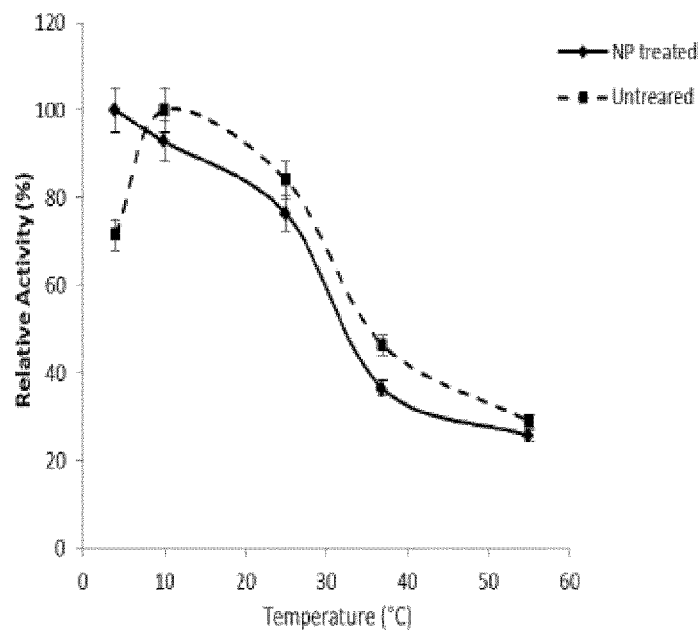
FIG. 1(A-D) are graphs comparing the temperature dependency of psychrophilic enzymes in presence and absence of nanoparticles (NP) (Hap NP for pectinase, cellulase, and xylanase; $Cu_2O$ NP for laccase). The enzymes are represented as follows: (A) pectinase; (B) laccase; (C) cellulase and (D) xylanase.
Figure 1:
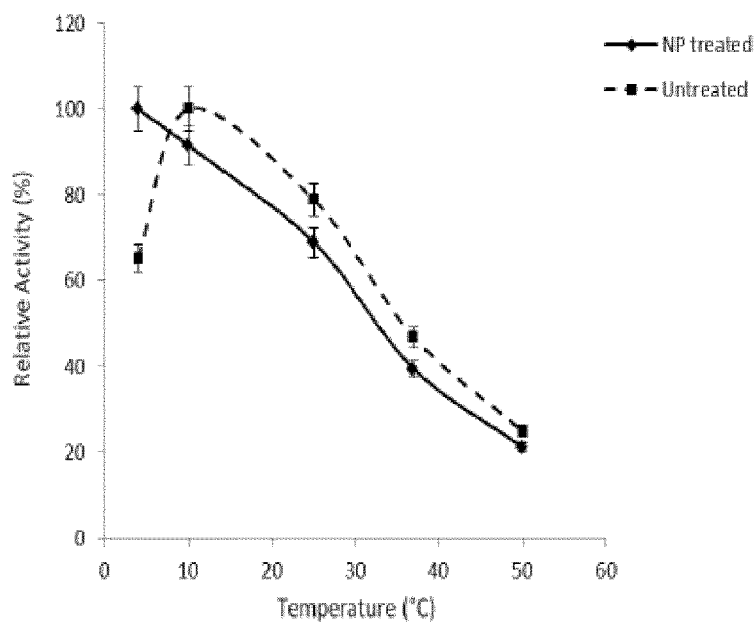
Figure 1:
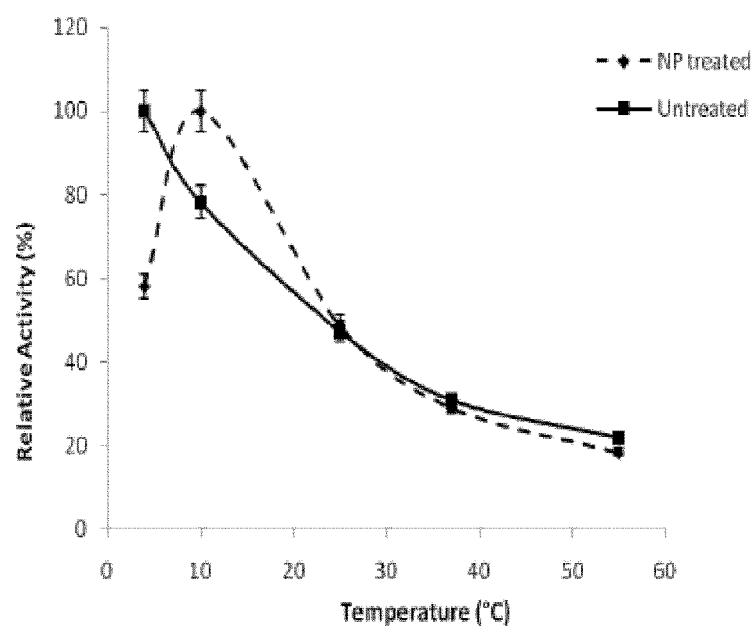
Figure 1:
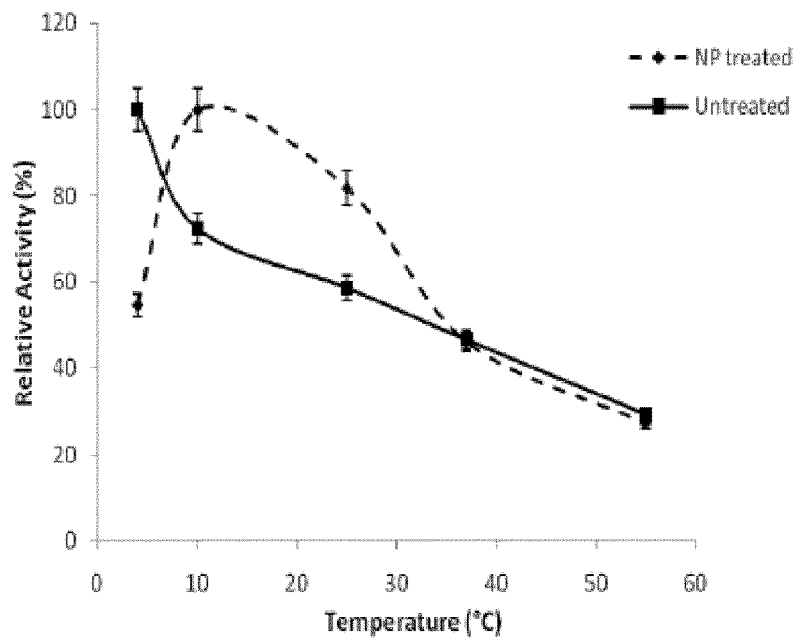

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Disclosed herein are compositions and methods related to the manufacture and use of stabilized psychrophilic enzymes. In some embodiments, the enzyme compositions and methods disclosed herein include (1) at least one psychrophilic enzyme; and (2) at least one nanoparticle in contact with the psychrophilic enzyme. In some embodiments, the nanoparticle is in contact with, but not linked to the psychrophilic enzyme. In some embodiments, the compositions can be used in industrial processes. For example, in some embodiments, the composition may be used to produce glucose and reducing sugars.

As used in this specification and the appended claims, the singular forms "a", "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "control" or "control enzyme," will have a meaning known to those of skill in the art and which will necessarily depend on the aspect of e.g., enzyme activity or conditions to be evaluated. Typically, a control or control enzyme will be compared to a test enzyme (for example, an enzyme that has been modified or treated in some way). The control and the test enzyme will typically be the same type of enzyme and will be derived from the same source. The control enzyme will not undergo the "modification" or "treatment" (for example, will not be contacted with nanoparticles, or will not be in a compositions comprising nanoparticles), but will be evaluated for enzymatic activity, pH tolerance, temperature tolerance, half-life, etc. under the same conditions as the "modified" or "treated" enzyme. Thus, the effects of the "modification" or "treatment" may be determined. In some embodiments, a "modification" or "treatment" includes contacting an enzyme with at least one nanoparticle, wherein the nanoparticle is not linked to the enzyme. In some embodiments, the enzyme and nanoparticle are in a composition.

As used herein the term "enhanced activity" or "increased activity" in the context of enzymes refer to an enhanced or increased number of moles of substrate converted to product per unit time as compared to a suitable control enzyme. In some embodiments, enhanced activity of an enzyme may be exhibited under "optimal" or "standard conditions" for a particular type of enzyme (for example, standard pH, standard temperature, standard substrate, etc.) as compared to a control enzyme under the same standard conditions. Additionally or alternatively, in some embodiments, enhanced activity may be exhibited under non-standard conditions for a particular type of enzyme (for example, at a higher or lower temperature, higher or lower pH, non-optimal substrate, etc.) as compared to a control enzyme under the same conditions, or as compared to a control enzyme under standard conditions. By way of example, but not by way of limitation, disclosed herein are psychrophilic enzymes in contact with but not linked to at least one nanoparticle, wherein the psychrophilic enzyme has enhanced activity as compared to a control psychrophilic enzyme (for example, the same type of psychrophilic enzyme not in contact with at least one nanoparticle, wherein the activity of the control enzyme is evaluated under the same conditions of temperature, buffer, pH, substrate, etc. as the psychrophilic enzyme in contact with the nanoparticles).

As used herein "enhanced half-life" or "increased half-life" with respect to enzymes refers to an enhancement or increase in the amount of time the enzyme can retain 50% of its activity as compared to the enzyme activity of a suitable control.

As used herein "enhanced thermal stability" or "increased thermal stability" or "enhanced temperature tolerance," in the context of enzymes refers to an enhancement or increase in structural and/or functional integrity, and/or enzyme activity at a higher temperature or a higher temperature range, which is outside the "normal" or "standard" temperature or temperature range for a given enzyme, as compared to a suitable control enzyme. By way of example, but not by way of limitation, in some embodiments of the compositions and methods disclosed herein, protease enzymes in contact with but not linked to at least one nanoparticle exhibit higher stability and/or activity at 40° C., 42° C., 44° C., 46° C., 48° C. and/or 50° C. as compared to a control protease enzyme (for example, an enzyme not in contact with at least one nanoparticle).

As used herein "enhanced psychrostability" or "increased psychrostability" in the context of enzymes refers to an enhancement or increase in structural and/or functional integrity, and/or enzyme activity at a lower temperature or a lower temperature range, which is outside the "normal" or "standard" temperature or temperature range for a given enzyme, as compared to a suitable control enzyme. By way of example, but not by way of limitation, in some embodiments of the compositions and methods disclosed herein, psychrophilic enzymes in contact with but not linked to at least one nanoparticle exhibit higher stability and/or activity at 2° C., 3° C., 4° C., 5° C., 6° C., 7° C., 8° C., 9° C., 10° C., 11° C., 12° C. or 13° C., 14° C. or 15° C. as compared to a control psychrophilic enzyme (e.g., an enzyme not in contact with at least one nanoparticle).

As used herein, "enhanced pH stability" or "enhanced pH tolerance" in the context of enzymes, refers to an enzyme which exhibits an increased or wider range of pH values in which the enzyme has activity (for example, any activity at all, or enhanced activity) as compared to a suitable control enzyme. By way of example, but not by way of limitation, an increased or a wider range of pH values can mean that the psychrophilic enzymes of the present technology (for example, enzymes in contact with but not linked to at least one nanoparticle) have more enzymatic activity at acidic pH as compared to suitable control enzymes, or that the psychrophilic enzymes of the present technology have more enzymatic activity at a more basic pH as compared to suitable control enzymes, or a combination of both.

As used herein, the term "linked to" with reference to "an enzyme being in contact with a nanoparticle but not linked to the nanoparticle" refers to intermolecular bonds that lead to immobilization of the nanoparticle on the enzyme or creates a permanent attachment of the nanoparticle to the enzyme.

As used herein, the term "nanoparticle" refers to any particle in which the largest dimension is in the nanometer range, and/or wherein the particles have an average size in the nanometer range. For example, in some embodiments, the nanoparticle has a largest dimension of, or a composition comprising a plurality of nanoparticles has an average dimension that is, less than 1000 nm, for example, about 999 nm, about 900 nm, about 800 nm, about 700 nm, about 600 nm, about 500 nm, about 400 nm, about 350 nm, about 300 nm, about 200 nm, about 100 nm, or ranges between any two of these values. Additionally or alternatively, in some embodiments, the largest dimension of the nanoparticle, or the average size of a plurality of nanoparticles is, for example, about 100 nm, about 90 nm, about 80 nm, about 70 nm, about 60 nm, about 50 nm, about 25 nm, about 20 nm, about 10 nm, about 5 nm, about 3 nm, about 2 nm, about 1 nm or less, or ranges between any two of these values.

As used herein, the term "protease" (also termed peptidase or proteinase) refers to an enzyme that conducts proteolysis, that is, begins protein catabolism by hydrolysis of the peptide bonds that link amino acids together in the polypeptide chain forming the protein.

As used herein, "psychrophilic enzymes" refer to those enzymes which have optimal function or activity at about 0° C. to 30° C. In some embodiments, the psychrophilic enzymes have optimal function or activity at temperature below about 10° C.

As used herein, the term "treated enzyme," "nanoparticle treated enzyme" and "enzyme composition" refer to compositions of the present technology including an enzyme in contact with, but not linked to, at least one nanoparticle. Additionally, treated enzyme, nanoparticle treated enzyme and enzyme composition, in some embodiments, refers to compositions of the present technology that include cell free extract from bacteria or live cells from bacteria in contact with, but not linked to, at least one nanoparticle. In some embodiments, the bacteria include, but is not limited to, psychrophilic bacteria, mesophilic bacteria, or a combination thereof.

I. Enzyme Compositions

Disclosed herein are methods and compositions comprising enzymes in contact with but not linked to at least one nanoparticle. In some embodiments, the enzymes in the compositions may exhibit one or more characteristics of enhanced activity, enhanced pH tolerance, enhanced temperature tolerance, and enhanced half-life as compared to a suitable control enzyme. In some embodiments, the enzymes of the present technology comprise psychrophilic enzymes. Additionally or alternatively, in some embodiments, the enzymes of the present technology comprise proteases.

In an alternative embodiment, the enzymes of the present technology are present in a cell free extract from bacteria. In some embodiments, the cell extract is from a psychrophilic bacteria, a mesophilic bacteria, or a combination thereof.

In an alternative embodiment, a plurality of live cells from bacteria are in contact with but not linked to at least one nanoparticle. In some embodiments, the live cells are from at least one psychrophilic bacteria, at least one mesophilic bacteria, or a combination thereof.

A. Psychrophilic Enzymes

The present technology is not limited by the type of psychrophilic enzyme, or the source of the enzyme. In some embodiments, psychrophilic enzymes may be isolated from natural sources (for example, from psychrophilic prokaryotic or eukaryotic organisms such as bacteria or molds) or may be prepared recombinantly. In some embodiments, the psychrophilic enzymes may be "wild-type" or may be mutant, and may include one or more amino acid substitutions, additions or deletions as compared to the wild-type enzyme.

Non-limiting examples of psychrophilic enzymes which may be used in the compositions and methods disclosed herein include pectinase, laccase, xylanase, cellulase, and combinations thereof.

B. Mesophilic Enzymes

The present technology is not limited by the type of mesophilic enzyme, or the source of the enzyme. In some embodiments, mesophilic enzymes disclosed herein may be isolated from natural sources (for example, from prokaryotic or eukaryotic organisms such as bacteria, yeast, molds, etc.) or may be prepared recombinantly. In some embodiments, the mesophilic enzyme may be "wild-type" or may be mutant, and may include one or more amino acid substitutions, additions or deletions as compared to the wild-type enzyme.

Non-limiting examples of mesophilic enzymes which may be used in the compositions and methods disclosed herein include protease.

C. Nanoparticles

The nanoparticles of the present technology are not limited by configuration, and can have any shape. For example, in some embodiments, nanoparticles may be substantially spherical. Additionally or alternatively, in some embodiments, nanoparticles can have a shape that is an ellipsoid, cube, cylindrical, or an irregular shape. Depending on the shape, the dimension described herein can refer to any of diameter, width, length, height, diagonal, and the like. Also, in the instance wherein the composition contains a plurality of nanoparticles, the dimension described herein can refer to an average of the individual dimensions of the plurality of the nanoparticles. For example, in some embodiments, the average of the individual dimensions of the plurality of nanoparticles is about 1000 nm, about 999 nm, about 900 nm, about 800 nm, about 700 nm, about 600 nm, about 500 nm, about 400 nm, about 300 nm, about 200 nm, about 100 nm, or ranges between any two of these values. Additionally or alternatively, in some embodiments, the average of the individual dimensions of the plurality of nanoparticles is, for example, about 100 nm, about 90 nm, about 80 nm, about 70 nm, about 60 nm, about 50 nm, about 25 nm, about 20 nm, about 10 nm, about 5 nm, about 3 nm, about 2 nm, about 1 nm, or ranges between any two of these values.

In some embodiments, the nanoparticle has a shape that is at substantially spherical and a diameter of about 2 nm to about 500 nm, about 10 nm to about 500 nm, about 25 nm to about 500 nm, about 50 nm to about 400 nm, about 100 nm to about 400 nm, about 80 nm to about 100 nm.

Exemplary, nanoparticles of the present disclosure include, but are not limited to, cuprous oxide nanoparticles, hydroxyapatite (HAp) nanoparticles, magnesium chloride nanoparticles, manganese chloride nanoparticles, calcium chloride nanoparticles, zinc nanoparticles, magnesium nanoparticles, manganese nanoparticles, or combinations thereof.

D. Forming Enzyme Compositions of the Present Technology

In some embodiments, the formation of an enzyme composition with enhanced activity, temperature tolerance, pH tolerance, half-life, etc., includes combining at least one psychrophilic enzyme or protease with at least one nanoparticle, wherein the nanoparticle is in contact with the psychrophilic enzyme or protease, but not linked to the psychrophilic enzyme or protease.

In some embodiments, the ratio of nanoparticles to psychrophilic enzyme (wt/wt) is about 1:4, or about 1:3, or about 1:2, or about 3:5, or about 1:1, or ranges between any two of these values. In some embodiments, the ratio of nanoparticles to protease (wt/wt) is about 1:4, or about 1:3, or about 1:2, or ranges between any two of these values.

In some embodiments, the mixture of nanoparticle and enzyme (i.e., a psychrophilic enzyme or protease) is vortexed. In some embodiments, vortexing is a pulse about 2 to 3 seconds. In some embodiments, the vortexing is performed at room temperature.

In some embodiments, the formation of an enzyme composition of the present technology includes combining cell free extract from bacteria with at least one nanoparticle. In some embodiments, the cell extract is from a psychrophilic bacteria, a mesophilic bacteria, or a combination thereof.

E. Characteristics of the Enzyme Compositions of the Present Disclosure

In some embodiments, the contact of an enzyme (for example, a psychrophilic enzyme or a protease) with a nanoparticles results in one or more of enhanced enzymatic activity, enhanced pH tolerance, enhanced temperature tolerance, increased half-life, and/or the ability to withstand multiple freeze-thaw cycles and maintain a given level of activity.

1. Enhanced Activity and Half-Life

In some embodiments, the enhanced activity or increased activity of a psychrophilic enzyme composition or protease composition of the present technology is determined by an increase in the maximum reaction velocity (Vmax), an increase in turnover number, i.e., the number of substrate molecule each enzyme site converts to product per unit time, and/or an increase in substrate affinity for example, a decrease in Michaelis Constant (Km), a decrease in the activation energy ($E_a$), or a combination thereof.

In some embodiments, the psychrophilic enzyme or protease in the composition of the present technology has a longer half-life and/or lower decay constant as compared to a control psychrophilic enzyme. In some embodiments, the longer half-life and/or lower decay constant improves the psychrophilic enzyme's or protease's productivity, as the enzyme remains active for longer durations during a lengthy reaction process.

In some embodiments, the psychrophilic enzyme or protease of the present technology retains enzymatic activity for a longer period of time as compared to the length of enzymatic activity of a control enzyme. In some embodiments, the psychrophilic enzyme composition or protease composition retains enzymatic activity for between about 1.5 hours to about 5 hours, or between about 2 hours to about 4.5 hours, or between about 2.5 hours to about 4 hours, or between about 3 hours to about 3.5 hours. In some embodiments, the duration of enzymatic activity of nanoparticle treated enzyme is about 1.5 hours, 2 hours, 3 hours, 4 hours, 5 hours, or ranges between any two of these values.

In some embodiments, the extended duration of enzymatic activity of nanoparticle treated enzymes as compared to control enzymes is observed at a temperature between about 2° C. to about 30° C., or from between about 4° C. to about 26° C., or from between about 6° C. to about 22° C., or from between about 10° C. to about 18° C., or from between about 12° C. to about 16° C. In some embodiments, the temperature in about 2° C., 4° C., 8° C., 12° C., 16° C., 20° C., 24° C., 28° C., or 30° C., or ranges between any two of these values.

2. Enhanced Activity of Psychrophilic Enzymes at Low Temperatures

In some embodiments, the present technology enhances the activity of psychrophilic enzymes at low temperatures. Psychrophilic enzymes are adapted to have high activity at low temperatures from about 0° C. to about 10° C. Additionally, psychrophilic enzymes often possess a higher specificity than their mesophilic counterparts. While psychrophilic enzymes are enzymatically active at very low temperatures, for example, below about 10° C., the contact of a psychrophilic enzyme with at least one nanoparticle increases the enzymatic activity of psychrophilic enzymes as compared to control psychrophilic enzymes.

In some embodiments, the enhanced activity of psychrophilic enzymes refers to enzyme activity at a temperature of about 0° C. to about 10° C., or from about 2° C. to about 8° C., or from about 4° C. to about 6° C. In some embodiments, the reference temperature in the context of nanoparticle-treated psychrophilic enzymes is about 0° C., 1° C., 2° C., 3° C., 4° C., 5° C., 6° C., 7° C., or 8° C., or 9° C., or 10° C., or ranges between any two of these values.

3. Enhanced Temperature Tolerance and Enhanced Activity of Protease

In some embodiments, the enzyme compositions of the present technology exhibit enhanced protease enzyme activity at "standard" temperatures, as well as at temperatures higher than the standard, or standard temperature range. Proteases, like many enzymes, denature and lose their enzymatic activity at higher temperatures. In some embodiments, the nanoparticle-treated proteases of the present technology have increased thermal stability and have higher enzymatic activity at higher temperatures compared to control proteases.

In some embodiments, the enhanced thermal stability of the nanoparticle treated protease refers to protease enzyme activity at a temperature range from about 40° C. to about 90° C., from about 45° C. to about 85° C., or from about 50° C. to about 80° C., or from about 55° C. to about 75° C., or from about 60° C. to about 70° C. In some embodiments, the temperature of reaction for a composition comprising nanoparticle-treated protease enzyme is about 40° C., 42° C., 45°

C., 50° C., 55° C., 60° C., 65° C., 70° C., 75° C., or 80° C., or 90° C., or ranges between any two of these values.

4. Enhanced pH Stability

In some embodiments, the present technology also provides enzyme compositions having enhanced pH stability. By way of example, but not by way of limitation, in some embodiments, a psychrophilic enzyme composition or protease composition of the present technology if functional under a greater or more extensive pH range as compared to a control enzyme. In some embodiments, the psychrophilic enzyme composition or protease composition shows more activity at a more acidic pH and/or a more basic pH as compared to a control enzyme. For example, a psychrophilic laccase treated with a copper-oxide nanoparticle showed optimal enzyme activity at about 5 pH to about 11 pH. The control laccase enzyme showed optimal enzyme activity at 7.5 pH to 10 pH.

5. Stabilization of Enzymes after Freeze-Thaw Cycles

In some embodiments, the psychrophilic enzyme compositions of the present technology have enhanced enzyme activity after three or more freeze-thaw cycles as compared to control enzymes. In some embodiments, the psychrophilic enzyme of the present technology maintains enzymatic activity up to 4 freeze-thaw cycles, 5 freeze-thaw cycles, 6 freeze-thaw cycles, 7 freeze-thaw cycles, 8 freeze-thaw cycles, or 9 freeze-thaw cycles. In some embodiments, the psychrophilic enzyme maintains enzymatic activity for more than 9 freeze-thaw cycles.

II. Methods for Using the Enzyme Compositions of the Present Technology

In some embodiments, at least one enhanced psychrophilic enzyme composition or protease composition is contacted with at least one substrate. In some embodiments, the contacting is performed at a temperature of about 0° C. to about 10° C., or from about 2° C. to about 8° C., or from about 4° C. to about 6° C. In some embodiments, the temperature of contacting, for example, for a psychrophilic enzyme composition, is about 0° C., 1° C., 2° C., 3° C., 4° C., 5° C., 6° C., 7° C., or 8° C., or 9° C., or 10° C., or ranges between any two of these values.

In some embodiments, the contacting is performed at a temperature about 40° C. to about 90° C., from about 45° C. to about 85° C., or from about 50° C. to about 80° C., or from about 55° C. to about 75° C., or from about 60° C. to about 70° C. In some embodiments, the temperature of contacting, for example, for a protease composition, is about 40° C., 37° C., 40° C., 42° C., 45° C., 50° C., 55° C., 60° C., 65° C., 70° C., 75° C., or 80° C., or 90° C., or ranges between any two of these values.

In some embodiments, the contacting is performed for about 1.5 hours to about 5 hours, about 2 hours to about 4.5 hours, about 2.5 hours to about 4 hours, or about 3 hours to about 3.5 hours. In some embodiments, the duration of enzymatic activity of nanoparticle treated enzyme is about 1.5 hours, 2 hours, 3 hours, 4 hours, 5 hours, or more, ranges between any two of these values.

In some embodiments, optimum production of product includes contacting for about 1 hour, or about 2 hours, or about 3 hours, or any ranges between any two of these values.

III. Kits

In some embodiments, kits are provided. In some embodiments, the kits include a first container comprising an enzyme, and a second container comprising nanoparticles. In some embodiments, the enzyme comprises a psychrophilic enzyme or a protease. In some embodiments, the psychrophilic enzymes include, but are not limited to, pectinase, laccase, cellulase, and xylanase. In some embodiments, the nanoparticle comprises one or more of cuprous oxide, hydroxyapatite (HAp), magnesium chloride, manganese chloride, and calcium chloride. In some embodiments, the kit also includes instructions to combine the nanoparticle and the enzyme.

In some embodiments, the kit includes a first container having one or more psychrophilic enzyme, a second container having one or more nanoparticles, and a third container having one or more protease. In some embodiments, the psychrophilic enzymes include, but are not limited to, pectinase, laccase, cellulase, and xylanase. In some embodiments, the nanoparticle comprises one or more of cuprous oxide, hydroxyapatite (HAp), magnesium chloride, manganese chloride, and calcium chloride. In some embodiments, the kit also includes instructions to combine the nanoparticle and psychrophilic enzyme. Additionally, in some embodiments, the kit also includes instructions to combine the nanoparticle and protease.

In some embodiments, the kit comprises an enzyme composition. In some embodiments, the kit includes a psychrophilic enzyme composition and/or a protease composition. In some embodiments, the psychrophilic enzyme kit includes a container having at least one psychrophilic enzyme combined with at least one nanoparticle. The nanoparticles are in contact with the psychrophilic enzyme, but are not linked to the psychrophilic enzyme. In some embodiments, the kit includes a container having at least one protease combined with at least one nanoparticle. The nanoparticles are in contact with the protease, but are not linked to the protease. In some embodiments, a kit includes both a psychrophilic enzyme composition and a protease enzyme composition.

In any of the kit embodiments disclosed above, in some embodiments, the kit includes instructions for treating a substrate with the enzyme compositions (for example, enzyme in contact with nanoparticles).

IV. Illustrative Uses of the Enzyme Compositions Disclosed Herein

A. General

The high activity of psychrophilic enzyme compositions of the present technology at low and moderate temperatures offers potential economic benefits, for example, through substantial energy savings in large-scale processes that would not require the expensive heating of reactors. Psychrophilic enzymes can also be useful in domestic processes. For instance, washing clothes at low temperatures can protect the colors of fabrics (and reduce energy consumption). In the food industry, their properties allow the transformation or refinement of heat-sensitive products, as example, cold-active pectinases can help to reduce viscosity and clarify fruit juices at low temperatures. The heat-lability of these enzymes also ensures their fast, efficient, and selective inactivation in complex mixtures.

Psychrophilic enzyme compositions of the present disclosure may also be used for the bioremediation of polluted soils and waste waters during the winter in temperate countries, when the degradative capacity of the endogenous micro-flora is impaired by low temperatures.

The psychrophilic enzyme compositions of the present technology are beneficial for their enhanced selectivity and high catalytic activity at low and moderate temperatures, in addition to their structural lability that can be exploited in multi-step processes requiring rapid and mild inactivation treatments. Furthermore, the inherent conformational plasticity of cold-adapted enzymes may be particularly suited to organic synthesis applications under the low water conditions used during the production of many fine chemicals and pharmaceutical intermediates.

The enzyme composition of the present technology can be used for a variety of purposes. For example, the composition provides robust catalytic alternatives for the breakdown of ligninocellulosic materials under industrial processing temperature. In some embodiments, the composition of the present technology can be used for bio-bleaching of fibers and cottons. The compositions can be used in the textile and paper industries in environmentally friendly methods. In some embodiments, the composition can be used for treatment of industrial wastewater containing phenolic, arylamine, diamine materials, and textile dye reagents. In some embodiments, the composition can be used for detoxification of industrial effluents. In some embodiments, the composition can be used for retting or bioscouring of natural bast fibers (for example, hemp and flax), and cotton fabric. In some embodiments, the composition can be used as an efficient tool for bio-remediation.

For example, in some embodiments, the composition can be used to treat a substrate, where the substrate includes a phenolic hydroxyl group by contacting and/or incubating the substrate with a composition. In some embodiments, the substrate comprises an azo group. In some embodiments, the substrate comprises syringaldazine, congo red, cotton blue, bromophenol blue, and malachite green. In some embodiments, the substrate comprises ortho and paradiphenols, aminophenols, polyphenols, polyamines, lignins and/or aryl diamines. In some embodiments, the substrate comprises a textile, wool, biocomposite, wastewater, paper, wood pulp, soil, animal feed, food, beverage, herbicide, pesticide, dye, pigment or combinations thereof. In some embodiments, the substrate comprises wood pulp comprising lignin.

In some embodiments, the substrate comprises dye or pigment, wherein the enzyme reacts with the dye or pigment and reduces the color of the substrate or decolorizes the substrate. In some embodiments, the substrate comprises a textile comprising a dye, wherein the enzyme reacts with the dye or pigment and reduces the color of the textile or decolorizes the textile. In some embodiments, the substrate comprises a beverage comprising phenolic compounds, wherein the enzyme reacts with the phenolic compound to reduce or remove browning or haze from the beverage. In some embodiments, the beverage is selected from fruit juice, beer, or wine.

In some embodiments, enzyme compositions disclosed herein comprising laccase may acts on phenolic substrates by catalyzing the oxidation of their phenolic hydroxyl groups to phenoxy radicals while dioxygen ($O_2$) is reduced to water. Enzymatic oxidation techniques have potential within a great variety of industrial fields including the pulp and paper, textile and food industries.

In some embodiments, enzyme compositions, disclosed herein, comprising pectinase enzyme, have a wide variety of uses. By way of example, but not by way of limitation, such enzyme compositions are useful in food processing, and for catalyzing chemical reactions that lead to quality improvement of food products. Enzyme compositions disclosed herein comprising pectinase have several uses in the paper and pulp industry, textile, fruit juice industries, etc.

In some embodiments, enzyme compositions, disclosed herein, comprising cellulases, are useful in various industries including pulp and paper, textile, laundry, biofuel production, food and feed industry, brewing, and agriculture. Due to the complexity of enzyme system and immense industrial potential, cellulases have been a potential candidate for research by both the academic and industrial research groups.

In some embodiments, enzyme compositions disclosed herein comprising xylanase are useful in biotechnology; exemplary uses include bio bleaching of wood pulp, treating animal feed to increase digestibility, processing food to increase clarification and converting lignocelluloses substances to feedstock and fuels.

In some embodiments, enzyme compositions disclosed herein comprising proteases are useful hydrolytic compositions, and are useful in detergents, foods pharmaceuticals, leathers, diagnostics, waste management and silver recovery. In some embodiments, the protease is a bacterial protease.

Exemplary, non-limiting uses of the enzyme compositions of the present technology are provided below.

B. Production of Glucose and Other Reducing Sugars at Low Temperatures

In some embodiments, the psychrophilic enzyme compositions described above can be used to produce glucose and other reducing sugars at low temperatures from a substrate. The use of the present technology may alleviate the need to require acid pre-treatment and/or high temperatures for reactions used in current methods for producing glucose and reducing from certain substrates.

In some embodiments, at least one protease in contact with at least one nanoparticle is contacted with at least one substrate. In some embodiments, the substrate includes, but is not limited to, de-seeded corn cob, de-seeded corn cob waste, ligno-cellulosic biomass, rice straws, and potato peels. In some embodiments, the nanoparticle includes, but is not limited to, cuprous oxide. In some embodiments, the protease is contacted with the substrate for about 1 hour, or about 2 hours, or about 3 hours, or any ranges between any two of these values. In some embodiments, the contacting is performed at a temperature between about 40° C. to about 90° C., or between about 50° C. to about 80° C., or between about 60° C. to about 70° C. Additionally, or alternatively, in some embodiments, the contacting is performed at a pH between about 5 to about 10, or between about 6 to about 9, or between about 7 to about 8.

The product from the incubation of nanoparticle-treated protease and substrate is subjected to another incubation with a psychrophilic enzyme composition of the present technology. In some embodiments, the psychrophilic enzyme composition of the present technology includes one or more psychrophilic enzyme in contact with but not linked to at least one nanoparticle. In some embodiments, the psychrophilic enzyme includes, but is not limited to, one or more of pectinase, laccase, cellulase, and xylanase. In another embodiments, the psychrophilic enzyme composition of the present technology includes a cell extract from psychrophilic bacteria in contact with but not linked to at least one nanoparticle. In some embodiments, the cell extract includes, but is not limited to, one or more of pectinase, laccase, cellulase, and xylanase. In yet another embodiments, the psychrophilic enzyme composition of the present technology includes live cells from psychrophilic bacteria in contact with but not linked to at least one nanoparticle.

In some embodiments, the nanoparticle includes, but is not limited to, cuprous oxide, HAp, or a combination thereof. In some embodiments, the psychrophilic enzyme composition is contacted with the substrate for about 0.5 hour, or about 1 hour, or about 1.5 hours, or about 2 hours, or any ranges between any two of these values. In some embodiments, the contacting is performed at a temperature of about 2° C. to about 15° C., or about 3° C. to about 12° C., or about 4° C. to about 8° C. Additionally, or alternatively, in some embodiments, the contacting is performed at a pH of about 6 to about 11, or about 7 to about 10, or about 8 to about 9.

C. Detergents and Cleaning Products

In some embodiments, the psychrophilic enzyme compositions disclosed herein may be used as detergents. In some embodiments, the detergents efficiently hydrolyze soils and stains at low temperatures, thereby reducing energy consumption, which results in decreased associated costs and environmental impacts. Additionally, garment alterations that take place during warm- and hot-water wash cycles, such as fabric degradation, shrinkage and dye bleeding, will be reduced. Given the trend of decreasing wash temperatures, particularly in Europe and Japan, the psychrophilic enzyme compositions of the present technology are capable of working efficiently under low to medium-temperature conditions in detergents.

For example, in some embodiments, the psychrophilic enzyme composition comprises a cellulase, and the composition is used to produce a cellulase-based detergent. Cellulase-based detergents comprising psychrophilic cellulase enzyme composition of the present technology have superior cleaning action without damaging fibers, improve color brightness and dirt removal, remove rough protuberances in cotton fabrics, and provide anti-redeposition of ink particles.

In some embodiments, the protease compositions of the present technology are useful in detergents for their ability to aid in the removal of proteinaceous stains and to deliver unique benefits that cannot otherwise be obtained with conventional detergent technologies. For example, in some embodiments, the detergents comprising a proteases composition of the present disclosure have improved performance/cost ratios, increased activity and improved compatibility with other detergent ingredients.

D. Paper Products and Paper Making

In some embodiments, the enzyme compositions of the present technology are used in paper making. Pulp and paper mills are beginning to use enzymes to solve problems in their manufacturing processes. Papermaking is essentially a continuous filtration process in which a dilute suspension of fibers, fiber fragments (fines), and inorganic filler particles, such as clay. Prominent among these polysaccharides are pectins, or polygalacturonic acids. The ability of polygalacturonic acids to complex cationic polymers (cationic demand) depends strongly on their degree of polymerization, monomers, dimers, and trimers of galacturonic acid do not cause measurable cationic demand, but hexamers and long chains have high cationic demand. Pectinase compositions of the present disclosure, for example, may be used to depolymerize polymers of galacturonic acids, and subsequently lower the cationic demand of pectin solutions and the filtrate from peroxide bleaching.

In some embodiments, the psychrophilic enzyme compositions of the present technology are used in the production of Japanese paper. For example, alkaline pectinase compositions of the present technology produced by *Bacillus* sp. and *Erwinia carotovora*, due to its strong macerating activity, is useful for retting of Mitsumata bast. These retted basts are used for the preparation of Japanese paper. In some embodiments, the strength of the pulp from bacterial retting using the compositions of the present disclosure is as high as that obtained by the conventional soda-ash cooking method. The paper sheets prepared from this pulp are very uniform and soft to touch.

The industrial preparation of paper includes separation and degradation of lignin in wood pulp. Environmental concerns are focused on replacing conventional and polluting chlorine-based delignification/bleaching procedures. Accordingly, the psychrophilic ligninolytic (lignin-degrading) enzymes (laccase) compositions of the present disclosure may be used for the (pre)treatment of lignocelluloses raw material such as wood chips in pulping; this is referred to as bio pulping. Bio-pulping using the enzyme compositions of the present technology is applicable to both mechanical and chemical pulps; advantages include reduced refining energy or increased mill throughput in mechanical pulping, and enhanced paper strength properties, alleviated pitch problems, improved yield, and reduced environmental impact in mechanical and chemical pulping and papermaking. In some embodiments, the enzyme compositions of the present technology can be applied in the industrial preparation of paper. For example, psychrophilic laccase compositions as disclosed herein have may be used to activate the fiberbound lignin during manufacturing of the composites, thus, resulting in boards with good mechanical properties without toxic synthetic adhesives. In some embodiments, laccase compositions of the present technology may be used to graft various phenolics acid derivatives onto Kraft pulp fibers. Additionally, psychrophilic xylanase enzyme compositions of the present disclosure may be useful in the removal of residual lignin from Kraft pulp. Residual ligin from the Kraft process is physically and chemically restricted by hemicelluloses. Lignin can link with hemicelluloses, and there has been isolation of lignin carbohydrate complexes from the Kraft pulp. Hemicellulose is a substrate of xylanase.

In some embodiments, the enzyme compositions of the present technology can be applied in the production of pulp and paper. For example, cellulase compositions as disclosed herein can be used as a co-additive in pulp bleaching; biomechanical pulping; improved draining; enzymatic deinking; reduced energy requirement; reduced chlorine requirement; improved fiber brightness, strength properties, and pulp freeness and cleanliness; improved drainage in paper mills; production of biodegradable cardboard, paper towels, and sanitary paper.

In some embodiments, the enzyme compositions of the present technology can be applied to the reduce paper industry environmental pollution. For example, chlorinated phenolic compounds as well as polychlorinated biphenyls, produced during conventional pulp bleaching, are toxic and highly resistant to biodegradation and form one of the major sources of environmental pollution. Xylanase compositions of the present disclosure can be used in a chlorine-free wood pulp bleaching process.

E. Wastewater and Waste Treatment

Paper and pulp mills, molasses based-alcohol distilleries, tanneries, dye-making units and textiles are some of the major industries that produce and discharge highly colored effluents. Each of these industrial effluents creates some specific problem besides producing aesthetically unacceptable intense coloring of soil and water bodies. They block the passage of light to the lower depths of the aquatic system resulting in cessation of photosynthesis, leading to anaerobic conditions, which in turn result in the death of aquatic life causing foul smelling toxic waters.

The pollution problems due to the industrial effluents have increased in the recent years. The dyeing processes have, in general, a low yield and the percentage of the lost dye in the effluents can reach up to 50%. For example, textile dye effluents are complex, containing a wide variety of dyes, natural impurities extracted from the fibers and other products such as dispersants, leveling agents, acids, alkalis, salts and sometimes heavy metals. In general, the effluent is highly colored with high biological oxygen demand (BOD), suspended solids (SS), toxicity, and chemical oxygen demand (COD), it has a high conductivity and is alkaline in nature. The degradation products of the dyes are often carcinogenic. To meet stringent environmental regulations, the wastewaters have to be treated before their discharge to the environment. Most currently existing processes to treat dye wastewater are ineffective and not economical. Therefore, the development of processes based on the composition comprising laccase as described above, seems an attractive solution due to their potential in degrading dyes of diverse chemical structure, including synthetic dyes currently employed in the industry. The enzyme compositions of the present technology, for example comprising laccase enzyme, are able to detoxify wastewater containing chlorophenols by catalyzing their polymerization via radical coupling. The coupling products can be removed from the wastewater by precipitation. Chlorophenols can also cross-couple and precipitate with other phenols present in wastewater, which may enhance their removal efficiency.

In some embodiments, the psychrophilic enzyme compositions of the present technology are used in the treatment of pectic wastewater. The wastewater from the citrus-processing industry contains pectinaceous materials that are barely decomposed by microbes during the activated-sludge treatment. Accordingly, pectinase-containing enzyme compositions of the present technology are useful to treat pectic wastewater.

F. Food, Beverage, Feed Industry, Pharmaceutical and Cosmetic

In some embodiments, the psychrophilic enzyme compositions disclosed herein are particularly attractive for the processing of foods due to their high catalytic activity at temperatures that minimize spoilage and alterations in taste and nutritional values. Their inherent low structural stability also facilitates inactivation once a desired product is attained.

Psychrophilic enzyme compositions of the present technology exhibit high catalytic activities at low and ambient temperatures and can also be exploited for the pharmaceutical industry. The increasing demand for enantiomerically-pure drugs and pharmaceutical intermediates has led to a rapid expansion of the use of biocatalysts in organic synthesis.

In the cosmetic industry, psychrophilic enzyme compositions of the present technology can enhance the yield of biotransformation involving volatile substrates, such as flavor and fragrance compounds subject to evaporation at high temperatures.

By way of example, but not by way of limitation, in some embodiments, the enzyme compositions of the present technology can be applied to processes that enhance or modify the color appearance of food, animal feed or beverages. The compositions of the present technology are useful in the elimination of undesirable phenolics, responsible for the browning, haze formation and turbidity development in clear fruit juice, beer and wine. In some embodiments, the compositions are used in different aspects of the food industry such as bioremediation, beverage processing, ascorbic acid determination, sugar beet pectin gelation, baking and as a biosensor.

In some embodiments, the psychrophilic enzyme compositions of the present technology are used in coffee and tea fermentation. For example, pectinases play an important role in coffee and tea fermentation. Fermentation of coffee using pectinolytic microorganisms is done to remove the mucilage coat from the coffee beans. Pectic enzymes are sometimes added to remove the pulpy layer of the bean, three fourths of which consists of pectin substances.

Fungal pectinases are also used in the manufacture of tea. Enzyme treatment accelerates tea fermentation, although the enzyme dose must be adjusted carefully to avoid damage to the tea leaf. The addition of pectinase also improves the foam-forming property of instant tea powders by destroying tea pectins.

In some embodiments, the enzyme compositions of the present technology can be applied in fermentation. For example, cellulase can be used for improving malting and mashing; improved pressing and color extraction of grapes; improved aroma of wines; improved primary fermentation and quality of beer; improved viscosity and filterability of worth; improved must clarification in wine production; improved filtration rate and wine stability.

In some embodiments, the enzyme compositions of the present technology can be applied in food production. For example, cellulase plays a role in the release of the antioxidants from fruit and vegetable pomace; improvement of yields in starch and protein extraction; improved maceration, pressing, and color extraction of fruits and vegetables; clarification of fruit juices; improved texture and quality of bakery products; improved viscosity fruit purees; improved texture, flavor, aroma, and volatile properties of fruits and vegetables; controlled bitterness of citrus fruits.

G. Biofuels

In some embodiments, enzyme compositions of the present technology are useful to make biofuels, such as ethanol made from the fermentation of carbohydrates produced in plants. Biofuels made with the compositions of the present technology represent a renewable energy source that can provide a myriad of other benefits, including increased energy security, a reduction in greenhouse gas emissions, economic benefits for rural communities, and mitigating problems associated with disposal of agro-industrial residues. All fuel ethanol is currently produced by fermentation of starchy crop-based sugars, industrial enzyme companies are pursuing methods for inexpensive ethanol production from low-cost lignocellulosic biomass, including agricultural waste, forestry waste, energy crops, and municipal solid waste. By way of example, but not by way of limitation, compositions comprising cold-adapted glycosyl hydrolases such as cellulases, xylanase and glycosidase of the present technology may enable cost-effective lignocellulose biomass conversion, thus facilitating the development of an economically-viable and renewable source of fuel to meet the world's increasing energy demands.

H. Enzyme Nanobiotechnology

In some embodiments, psychrophilic enzymes compositions of the present technology are useful for synthesizing nanostructured materials at low temperatures and mild conditions. This results in inexpensive, environmentally-friendly alternatives to traditional synthesis techniques.

I. Exemplary Applications Using Laccase

Laccases can act on a wide range of substrates. It has the ability to oxidize both phenolic and nonphenolic lignin related compounds as well as highly recalcitrant environmental pollutants, which makes them very useful for their application to several biotechnological processes. Such applications include the detoxification of industrial effluents, mostly from the paper and pulp, textile and petrochemical industries, use as a tool for medical diagnostics and as a bioremediation agent to clean up herbicides, pesticides and certain explosives in soil. Laccases are also used as cleaning agents for certain water purification systems, as catalysts for the manufacture of anti-cancer drugs and even as ingredients in cosmetics. In addition, their capacity to remove xenobiotic substances and produce polymeric products makes them a useful tool for bioremediation purposes.

1. Laccasse in the Degradation of Lignocellulosic Materials

The compositions of the present technology comprising laccase are useful in degrading lignocellulosic materials. The compositions can be used, for example, to initiate a series of redox reactions, which degrade the lignin (or lignin-derived pollutants). The compositions can be used to oxidize aromatic compounds until the aromatic ring structure is cleaved, which can then be followed by additional degradation with other enzymes. The breakdown of lignocellulosic materials has wide variety of industrial applications.

Enzymatic hydrolysis of lignocellulosic materials is the first step for either digestion to biogas (methane) or fermentation to ethanol. Ethanol is an important renewable bio-fuel in terms of volume and market value. The demand for ethanol has a significant market, as ethanol is commonly used as a chemical feedstock or as an octane enhancer or petrol additive. Hence, the compositions of the present technology are useful in the production of ethanol from ligninocellulosic materials.

Biogas is another energy source that is used as car fuel, or for production of heat or electricity. Pretreatment of ligninocellulosic materials with the compositions of the present technology would degrade the ligninocellulosic materials and help to produce ethanol and biogas.

Bioconversion of lignocellulosic breakdown wastes could make a significant contribution to the production of organic chemicals.

In some embodiments, the composition of the present technology can be used to produce vanillin. Vanillin is an exemplary bio-product of lignin breakdown. The largest use of vanillin is as a flavoring, usually in sweet foods. It is used in the flavor industry, as a very important key note for many different flavors, especially creamy profiles. The ice cream and chocolate industries together comprise 75% of the market for vanillin as a flavoring, with smaller amounts being used in confections and baked goods. Vanillin is also used in the fragrance industry, in perfumes to mask unpleasant odors or tastes in medicines, livestock fodder, and cleaning products. Vanillin has been used as a chemical intermediate in the production of pharmaceuticals and other fine chemicals.

2. Laccase in Organic Synthesis

In some embodiments, the composition of the present technology comprising laccase can be employed for several applications in organic synthesis, e.g., the oxidation of functional groups, the coupling of phenols and steroids.

In some embodiments, the composition of the present technology comprising laccase can be used to aerobically convert phenol to catechol. Catechol is the precursor to pesticides, flavors, and fragrances. Approximately 50% of synthetic catechol is consumed in the production of pesticides, the remainder being used as a precursor to fine chemicals such as perfumes and pharmaceuticals.

Catechol is a common building block in organic synthesis. Several industrially significant flavors and fragrances are prepared starting from catechol. Guaiacol is prepared by methylation of catechol and is then converted to vanillin. The related monoethyl ether of catechol, guethol, is converted to ethylvanillin, a component of chocolate confectioneries. 3-Trans-Isocamphylcyclohexanol, widely used as a replacement for sandalwood oil, is prepared from catechol via guaiacol and camphor. Piperonal, a flowery scent, is prepared from the methylene diether of catechol followed by condensation with glyoxal and decarboxylation.

The compositions of the present technology are useful to oxidize phenolic compounds (e.g., phenols, polyphenols, and meta substituted phenols), diamines and a variety of other components utilizing molecular oxygen. In some embodiments, the compositions of the present technology are useful in the synthesis of quinones by oxidizing phenols and catechols. A large scale industrial application of quinones is for the production of hydrogen peroxide. 2-Alkylanthraquinones are hydrogenated to the corresponding hydroquinones (quinizarins), which then transfer $H_2$ to oxygen.

Derivatives of quinones are common constituents of biologically relevant molecules (e.g., Vitamin K1 is phylloquinone). Natural or synthetic quinones show a biological or pharmacological activity, and some of them show antitumoral activity and possess a number of biological properties, including some claims in herbal medicine. These applications include purgative (sennosdes), anti-microbial (rhein- and saprorthoquinone), anti-tumor (emodin and jugone), inhibition of PGE2 biosynthesis (arnebinone and arnebifuranone) and anti-cardiovascular disease (tanshinone).

Many natural and artificial coloring substances (dyes and pigments) are quinone derivatives. They are second only to azo dyes in importance as dyestuffs, with particular emphasis on blue colors. Alizarin (2,3-dihydroxy-9,10-anthraquinone), extracted from the madder plant, was the first natural dye to be synthesized from coal tar.

3. Exemplary Use of Lacasse in Textile Industries

The thermostable laccase enzymes of the present technology, with enhanced activity at higher temperatures and decreased pH dependency, are also useful in wool dyeing, rove scouring, anti-shrink treatment of wool, and dye synthesis.

In textile processing, laccase enzymes of the present technology can be used for improving the fabric whiteness in bleaching process, de-colorization of dyed textile materials and colored effluent and scouring of fibers, wool dyeing, and wool anti-felting. Laccase enzymes of the present technology can be used to color wool fabric that was previously padded with hydroquinone. Laccase enzymes of the present technology can be used for wool dyeing. A dye bath can be prepared with a dye precursor (2, 5-diaminobenzene-sulfonic acid), dye modifiers (catechol and resorcinol) and laccase, without any dyeing auxiliaries.

Laccase enzymes of the present technology are useful for reducing felting shrinkage of wool fabric. Increasing concentration of laccase can lead to a decrease in fabric shrinkage.

Laccase enzymes of the present technology can be used for roving treatment to improve yarn regularity. The advantage of the use of laccase in rove scouring is that the process is performed under mild reaction conditions resulting, thus, in an ecologically friendly process.

Laccase enzymes of the present technology can be used to form red azo dyes by the oxidative coupling of 3-methyl-2-benzothiazolinone hydrazone (MBTH) and phenols. Oxidation of ferulic acid by laccase in a biphasic hydro-organic medium leads to the production of stable yellow colored products.

a. Denim Finishing

In the textile finishing industry, enzymatic degradation of indigo could have potential both in stone-wash process and for the treatment of dyeing effluents. Several steps are involved in the manufacture of denim garments between dyeing and the final stone-washing where excessive amounts of indigo are removed from the fabrics and discharged with the wastewater. The fabrics are partially bleached by a treatment with sodium hypochlorite, followed by neutralization and a rinsing step all causing substantial environmental pollution. The enzyme compositions of the present technology, for example having the laccase enzyme, are useful in denim finishing.

b. Cotton Bio-Bleaching

The purpose of cotton bleaching is to decolorize natural pigments and to confer a pure white appearance to the fibers. Mainly flavonoids are responsible for the color of cotton. The most common industrial bleaching agent is hydrogen peroxide. However, radical reactions of bleaching agents with the fiber can lead to a decrease in the degree of polymerization and, thus, to severe damage. Furthermore, a huge amount of water is needed to remove hydrogen peroxide from fabrics, which can cause problems in dyeing. Therefore, replacement of hydrogen peroxide by an enzymatic bleaching system would not only lead to better product quality due to less fiber damage but also to substantial savings on washing water needed for the removal of hydrogen peroxide.

In some embodiments, the enzyme compositions of the present technology are used to enhance the bleaching effect on cotton fabrics. For example, it has been reported that the bleaching effect is enhanced on cotton fabrics by using laccase in low concentrations. Also, the composition of the present technology comprising laccase can improve the whiteness of cotton due to oxidation of flavonoids. For example, studies have shown that a laccase from a newly isolated strain of *T. hirsuta* was responsible for whiteness improvement of cotton most likely due to oxidation of flavonoids. In addition, the short time of the enzymatic pre-treatment sufficient to enhance fabric whiteness makes this bio-process suitable for continuous operations.

J. Applications Using Cellulase

1. Cellulase in Agriculture

In some embodiments, the enzyme compositions of the present technology can be applied in agriculture. Plant pathogen and disease control; generation of plant and fungal protoplasts; enhanced seed germination and improved root system; enhanced plant growth and flowering; improved soil quality; reduced dependence on mineral fertilizers.

2. Cellulase in Bioconversion

In some embodiments, the enzyme compositions of the present technology can be applied in bioconversion. For example, conversion of cellulosic materials to ethanol, other solvents, organic acids and single cell protein, and lipids; production of energy-rich animal feed; improved nutritional quality of animal feed; improved ruminant performance; improved feed digestion and absorption; preservation of high quality fodder.

3. Cellulase in Textile Industry

In some embodiments, the enzyme compositions of the present technology can be applied in the textile industry. For example, bio-stoning of jeans; bio-polishing of textile fibers; improved fabrics quality; improved absorbance property of fibers; softening of garments; improved stability of cellulosic fabrics; removal of excess dye from fabrics; restoration of color brightness.

4. Others Applications Using Cellulase

In some embodiments, the enzyme compositions of the present technology, wherein the enzyme is cellulase, can be used in one of the following: improved carotenoids extraction; improved oxidation and color stability of carotenoids; improved olive oil extraction; improved malaxation of olive paste; improved quality of olive oil; reduced risk of biomass waste; production of hybrid molecules; production of designer cellulosomes.

K. Exemplary Applications Using Xylanase

In some embodiments of the present technology, compositions comprising xylanase are used. Exemplary uses include, but are not limited to bioleaching of wood pulp, treating animal feed to increase digestibility, processing food to increase clarification and converting lignocellulosic substances to feedstock and fuels.

1. Bioleaching

In some embodiments, the enzyme compositions of the present technology can be applied in bioleaching. Conventional bleaching of chemical pulp to a higher brightness without complete removal of lignin has not been successful. Conventionally, chlorine is used for bleaching. Accordingly, compositions of the present technology including xylanase are useful for bio-bleach.

2. Others Exemplary Applications Using Xylanase

Additional areas in which the present enzyme technology comprising xylanase is useful include, but are not limited to, use as food additives for poultry, in wheat flour for improving dough handling and quality of baked products, for the extraction of coffee, plant oils, and starch, in the improvement of nutritional properties of agricultural silage and grain feed, and in combination with pectinase and cellulase compositions for clarification of fruit juices and degumming of plant fiber sources such as flax, hemp, jute, and ramie.

L. Exemplary Applications Using Pectinase

In some embodiments, psychrophilic pectinase enzyme compositions of the present technology are useful in the fruit and textile industries. Psychrophilic pectinase enzyme compositions of the present technology break down complex polysaccharides of plant tissues into simpler molecules like galacturonic acids. In some embodiments, psychrophilic acidic pectinases enzyme compositions of the present technology are useful to bring down the cloudiness and bitterness of fruit juices. In some embodiments, psychrophilic acidic pectinases enzyme compositions of the present technology are useful in the textile industry for the retting and degumming of fiber crops, production of good quality paper, fermentation of coffee and tea, oil extractions and treatment of pectic waste water.

Pectate lyase is an alkaline enzyme. In some embodiments, psychrophilic pectate lyase enzyme compositions of the present technology are useful in the degumming and retting of fiber crops and pretreatment of pectic wastewater from fruit juice industries. Typically, these enzymes come mostly from bacterial sources. In the industrial sector, psychrophilic alkaline pectinase compositions of the present disclosure, mainly from *Bacillus* sp. are applied for the following purposes.

1. Retting and Degumming of Fiber Crops

In some embodiments, the enzyme compositions of the present technology are used in retting and degumming of fiber crops. For example, pectinolytic enzymes are involved in the retting and degumming of jute, flax, hemp, ramie, kenaff (*Hibiscus sativa*) and coir from coconut husks. Retting is a fermentation process in which certain bacteria (e.g., *Clostridium, Bacillus*) and certain fungi (for example, *Aspergillus, Penicillium*) decompose the pectin of the bark and release fiber.

Ramie fibers are an excellent natural textile, but decorticated ramie fibers contain 20±35% ramie gum, which mainly consists of pectin and hemicellulose; hence it is necessary to degum fibers for meeting the requirement for textiles.

2. Oil Extraction

In some embodiments, the enzyme compositions of the present technology are used in oil extraction. Oils from rape seed (canola), coconut germ, sunflower seed, palm, kernel and olives are traditionally produced by extraction with organic solvents. The most commonly used solvent is hexane, which is a potential carcinogen. Cell-wall-degrading enzymes, including pectinase, may be used to extract vegetable oil in an aqueous process by liquefying the structural cell wall components of the oil-containing crop.

EXAMPLES

The present technology is further illustrated by the following examples, which should not be construed as limiting in any way.

Example 1. Isolation of Industrial Enzymes Secreting Bacteria from Soil

Isolation of Enzymes

Pectinase, laccase, cellulolytic, and xylanase secreting bacteria were isolated from Himalayan forest soil, which is found at 3800 meters above sea level.

The pectinolytic bacterial strain was isolated by the "Ruthenium red" method. In this method, several bacterial colonies were formed on YP agar plates. The YP plates were flooded by ruthenium red solution. Those colonies that showed a halo were identified as a pectinolytic strain.

The laccase secreting bacterial strain was isolated by the "Syringaldazine" method. Bacterial colonies were formed on Luria-Agar (LA) plates, which were flooded by Syringaldazine solution. Those bacterial colonies that formed purple coloration were identified as laccase secreting bacteria.

The xylanase secreting bacterial strain was isolated by the "Congo red" method. Bacterial colonies were grown on xylan-agar plates. Bacterial colonies that formed on the xylan-agar plates were flooded with congo-red solution. Those bacterial colonies that formed a halo were identified as xylanase secreting bacteria.

The cellulolytic bacterial strain was isolated by the "Congo red" method. Bacterial colonies were grown on CMC-agar plates. Bacterial colonies, formed on the CMC-agar plate were flooded by congo-red solution. Those bacterial colonies formed halo were identified as cellulolytic secreting bacteria.

Every bacterial culture was incubated at 20° C.

Partial Purification of Enzymes

Pectinase enzyme was partially purified by two consecutive processes. First, and primarily, by ion exchange chromatography (CM Sepharose®; Sigma-Aldrich) and then followed by gel filtration chromatography (Sephadex® G-75; Sigma-Aldrich).

Laccase enzyme was partially purified by three consecutive processes. First, and primarily, by 30-80% ammonium sulphate cut method, followed by ion exchange chromatography (CM Sepharose®; Sigma-Aldrich), and finally by gel filtration chromatography (Sephadex® G-75; Sigma-Aldrich).

Cellulase enzyme was partially purified by two consecutive processes. First, and primarily, by ion exchange chromatography (DEAE cellulose; Sigma-Aldrich) and then followed by gel filtration chromatography (Sephadex® G-100; Sigma-Aldrich).

Xylanase enzyme was partially purified by two consecutive processes. First, and primarily, by ion exchange chromatography (CM Sepharose®; Sigma-Aldrich) and then followed by gel filtration chromatography (Sephadex® G-50; Sigma-Aldrich).

Example 2. Measurement of Enzyme Activities

Purified pectinase was incubated with poly-galacturonic acid (PGA) in 25 mM tris-Cl buffer (pH-8.5) for 2 hours at 20° C. by TBA method. After two hours of incubation of the enzyme-substrate complex, the red color formation was measured at 550 nm.

The laccase activity was determined by syringaldazine assay, which measured absorbance at 525 nm. About 1 ml laccase enzyme was added to 3 ml of 25 mM tris-Cl buffer, pH: 8.5, and then 2 ml substrate syringaldazine solution (in methanol at 1:2 diluted with Dioxan) was added to make the total assay system 5 ml. The syringaldazine assay was performed at 20° C.

Cellulase assay was performed by dinitrosalicylic acid method. 1 ml of culture filtrate placed in a test tube and diluted to 2 ml with distilled water. Tris-Cl buffer of pH 7.5 was used with CMC as the substrate. Next, 3 ml of DNS reagent was added to the prepared culture filtrate. The contents in the test tubes were heated in a boiling water bath for 5 min. After heating, the contents were cooled at room temperature. At the time of cooling, 7 ml of freshly prepared 40% sodium potassium tartarate solution was added. After cooling, the samples were read at 510 nm in a U.V. spectrophotometer. The amount of reducing sugar was determined using a standard graph of glucose.

Xylanase activity was assayed using 1% solution of Birchwood xylan as the substrate and the amount of reducing sugars released was determined by the dinitrosalicylic acid method. Tris-Cl buffer of pH 8.0 was used for performing the assay. One unit of enzyme activity was defined as 1 mM xylose equivalent produced per minute under the given conditions. The samples were read at 410 nm in a U.V. spectrophotometer.

Example 3. Effect of Treating Psychrophilic Enzymes with Nanoparticles

Method and Materials $Cu_2O$ nanoparticles ($Cu_2O$ NP) and hydroxyapatite nanoparticles (HAp NP) were purchased from Sigma-Aldrich (Accession Nos: 678945, 702153 respectively).

Buffer used was Tris-Cl of pH 8.5, pH 8, pH 7.5 for pectinase and laccase, xylanase, and cellulase, respectively.

Enzymes were mixed with nanoparticles as follows: HAp NP for pectinase, cellulase and xylanase and Cu2O NP for laccase enzyme. Pectate lyase, cellulase, and xylanase were combined with 8.8 µg/ml, 11 µg/ml and 6.6 µg/ml of HAp NP, respectively. Laccase was combined with 0.1 mM Cu2O NP.

Nanoparticles and the enzyme were mixed by vortexing for about 2 to 3 seconds at room temperature, before pre-incubation.

Total reaction volume (enzyme, buffer, substrate, and nanoparticle) was 1 ml for each sample.

Enzyme activities were assayed according to protocols detailed in Example 2.

After initial pre-incubation, detailed in Table 1, the assay for every enzyme system was performed at 20° C. The incubation time for pectinase was 2 hours, for laccase it was 5 minutes, for xylanase it was 30 minutes and for cellulase it was 20 minutes.

TABLE 1

Psychrophilic enzymes and respective incubation periods and substrates

| Enzyme | Substrate | Pre-incubation Temp. (° C.) | Incubation pH | Incubation Time (minutes) | Freeze thaw cycles | Absorbance (nm) |
|---|---|---|---|---|---|---|
| Pectinase | Apple Pectin | 55, 37, 25, 10 and 4 | (3-10) | (30-300) | 7 | 550 |
| Laccase | Syringaldazine | 55, 37, 25, 10 and 4 | (3-10) | (5-120) | 7 | 525 |
| Xylanase | Birchwood xylan | 55, 37, 25, 10 and 4 | (3-10) | (60-300) | 7 | 410 |
| Cellulase | Carboxy-Methyl-Cellulose | 55, 37, 25, 10 and 4 | (3-10) | (30-180) | 7 | 510 |

Study of Enzyme Characteristics in Presence and Absence of Nanoparticles

Temperature: The use of enzymes in industrial processes may benefit from reactions at low temperatures, for example, in order to improve productivity. This implies that the enzyme needs to be active at lower temperatures. To measure the temperature dependency, all four enzymes were incubated at five different temperatures: 55° C., 37° C., 25° C., 10° C. and 4° C. The temperature dependency was measure in presence and absence of nanoparticles (HAp NP was added to pectinase, cellulase and xylanase assay system, $Cu_2O$ NP was added to laccase assay system).

pH: The use of enzymes in industrial processes often require reactions at different pH in order to improve interaction with different substrate. This implies that the enzyme is active at different pH scales. To measure the temperature dependency, all four enzymes were incubated from pH 3-10. The pH dependency was measured in presence and absence of the corresponding nanoparticles used with the enzymes.

Time: The use of enzymes in industrial processes often requires performing reactions for a long time span in order to improve productivity. To measure the time kinetics, pectinase was incubated for 30-300 minutes, laccase was incubated for 5-120 minutes, cellulase was incubated for 1-5 hours, and xylanase for 30-180 minutes. The time kinetics was measured in presence and absence of the corresponding nanoparticles of those enzymes.

Results:

Nanoparticle (HAp and $Cu_2O$) Supplementation Enhances the Cold Resistance of Psychrophilic Enzymes When incubating the enzymes with its substrate and varying temperature from higher to lower, only nanoparticle treated enzymes (absence of Cu and Ca ion in buffer) showed significantly higher activity than only metal (Cu and Ca) ion (without nanoparticle) supplemented enzymes. Moreover, only nanoparticle treated enzymes showed higher activity than both metal ion supplemented (in buffer) and nanoparticle treated enzymes:

1) Only Cu—NP>Cu—NP+$Cu^{2+}$ Only Cu—NP>$Cu^{2+}$
2) Only Ca—NP>Ca—NP+$Ca^{2+}$ Only Ca—NP>$Ca^{2+}$ It was observed that in absence of NP, pectinase showed the optimum temperature of 10° C., whereas in presence of 8.8 μg/ml HAp NP, the optimum temperature became 4° C. FIG. 1A. Laccase, in the absence of NP, the optimum temperature was 10° C., whereas in presence of 0.1 mM $Cu_2O$ NP, the optimum temperature became 4° C. FIG. 1B. Cellulase, in the absence of NP, the optimum temperature was 7° C., whereas in presence of 11 μg/ml HAp NP, the optimum temperature became 4° C. FIG. 1C. For xylanase the optimum temperature was 8° C., whereas in presence of 8.8 μg/ml HAp NP, the optimum temperature became 4° C. FIG. 1D.

NP supplementation made all the psychrophilic enzymes more enzymatically active at 4° C. than the control enzyme.

Nanoparticle Supplementation Enhanced the pH Range of Laccase Activity

Figure 2:
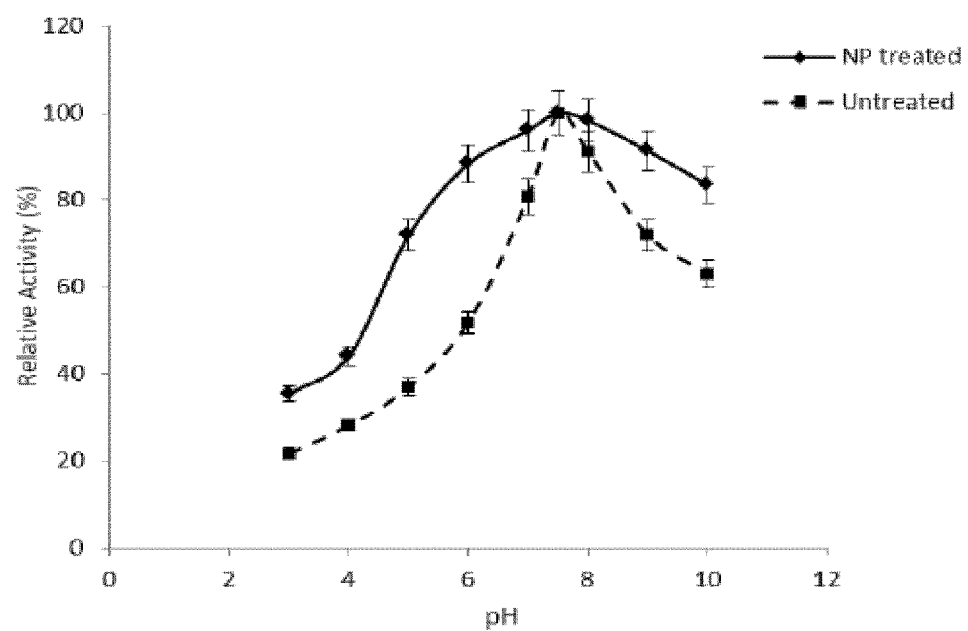
FIG. 2 is a graph illustrating that NP supplementation enhances pH dependency range of psychrophilic laccase.

The pH dependence of laccase activity was assessed in the presence and absence of copper-oxide nanoparticle. It was found that NP treated laccase showed activity at both acidic and basic pH. Between the pH values of 6 to 10 laccase was active in the presence of NP. Whereas untreated laccase activity was optimum at pH 7.5 to 10. FIG. 2.

Nanoparticle Supplementation Promotes Retention of Psychrophilic Enzyme Activity at Low Temperature.

Figure 3:
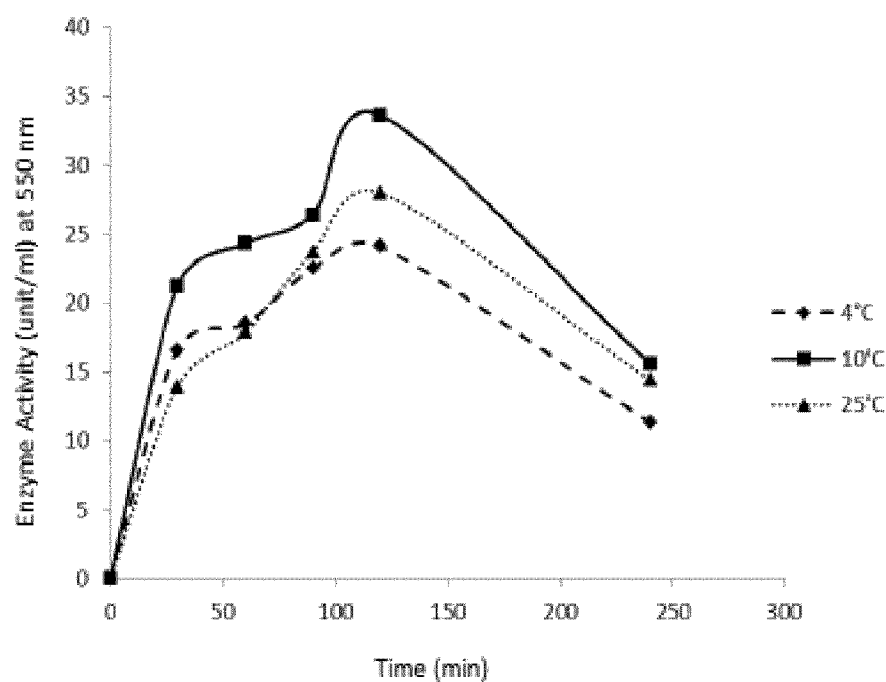
FIG. 3(A-H) are graphs comparing the time kinetics of psychrophilic enzymes at three different temperature (4° C., 10° C. and 25° C.) in the presence and absence of NP, (A) Untreated pectinase; (B) NP treated pectinase; (C) Untreated laccase; (D) NP treated laccase; (E) Untreated cellulase; (F) NP treated cellulase; (G) Untreated xylanase; (H) NP treated xylanase.
Figure 3:
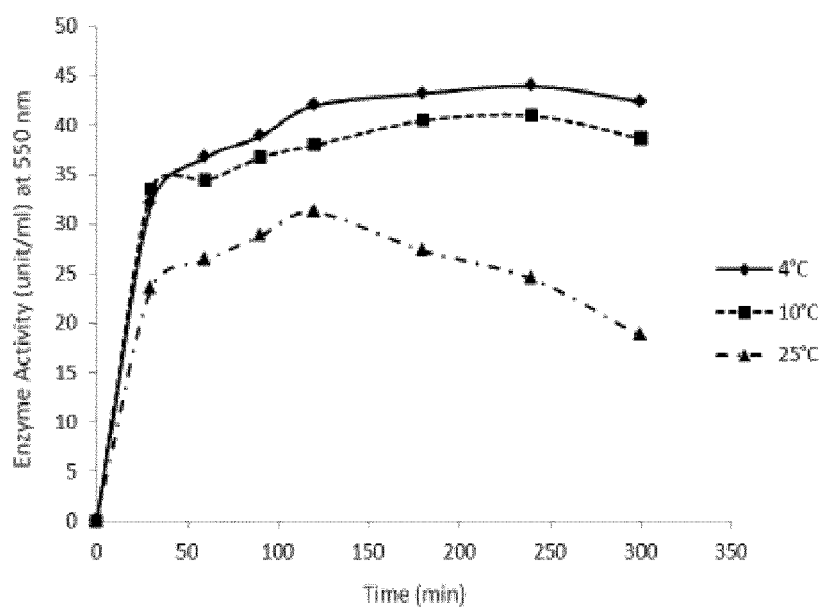
Figure 3:
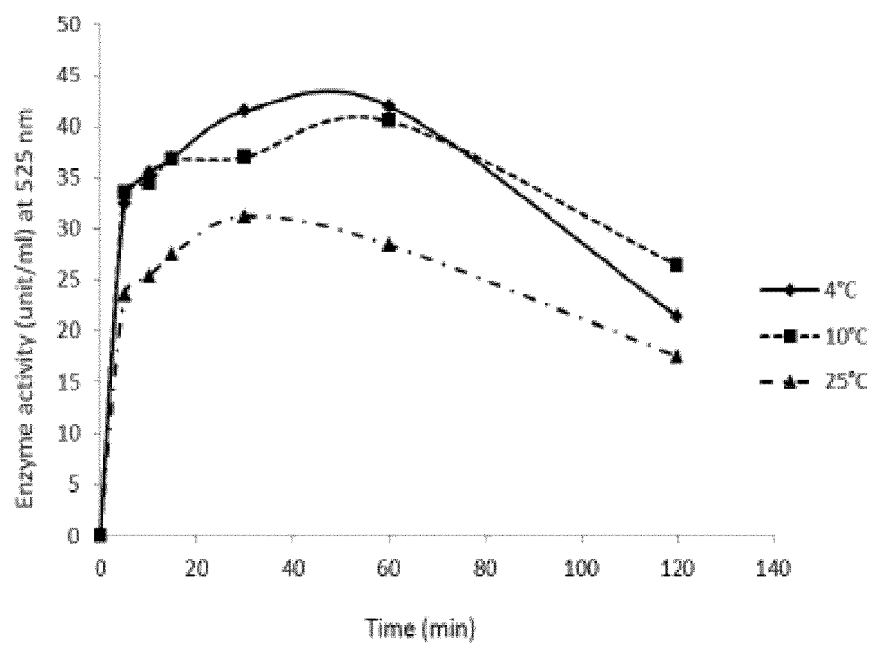
Figure 3:
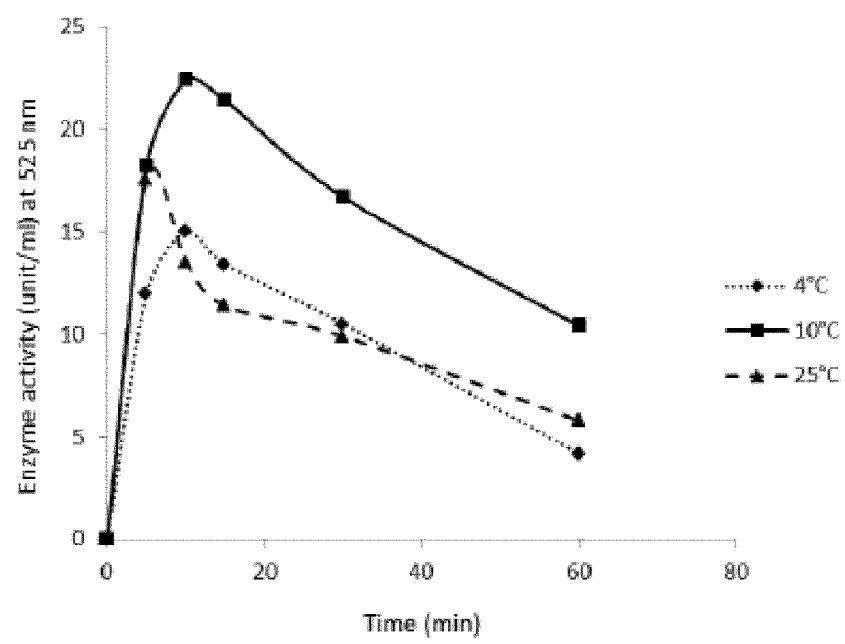
Figure 3:
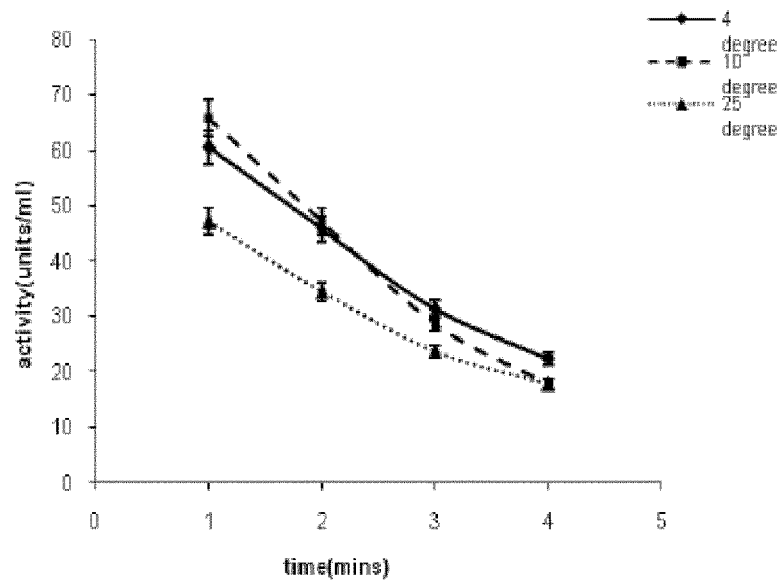
Figure 3:
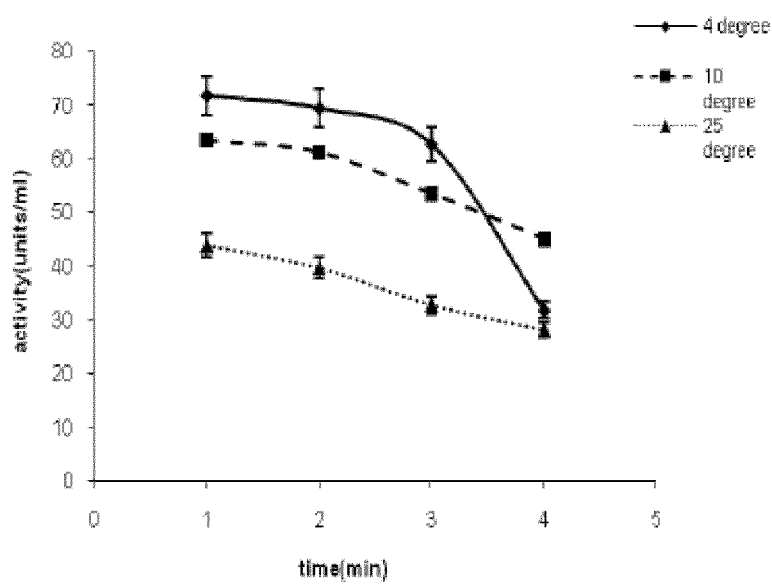
Figure 3:
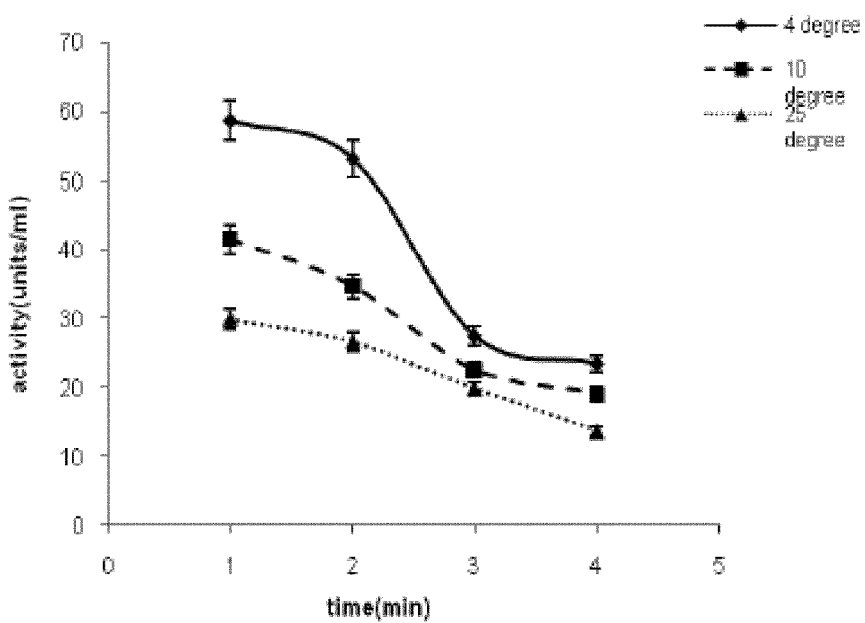
Figure 3:
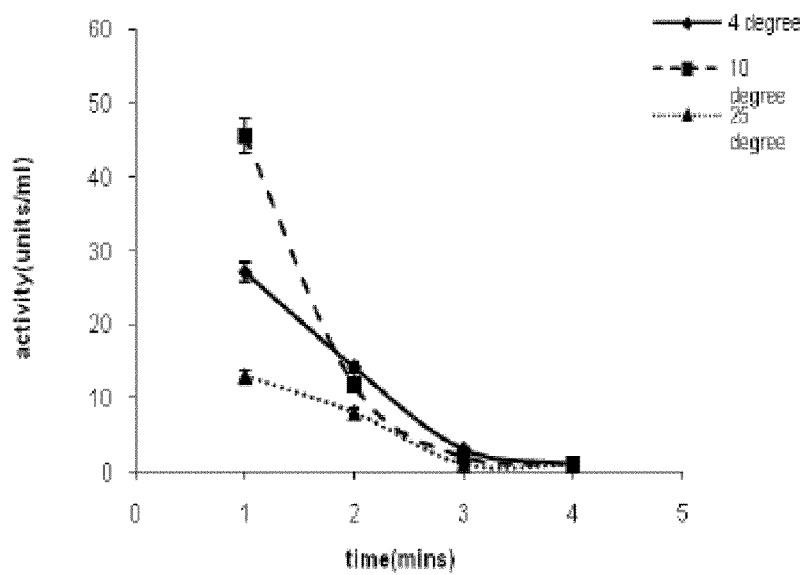
Figure 4:
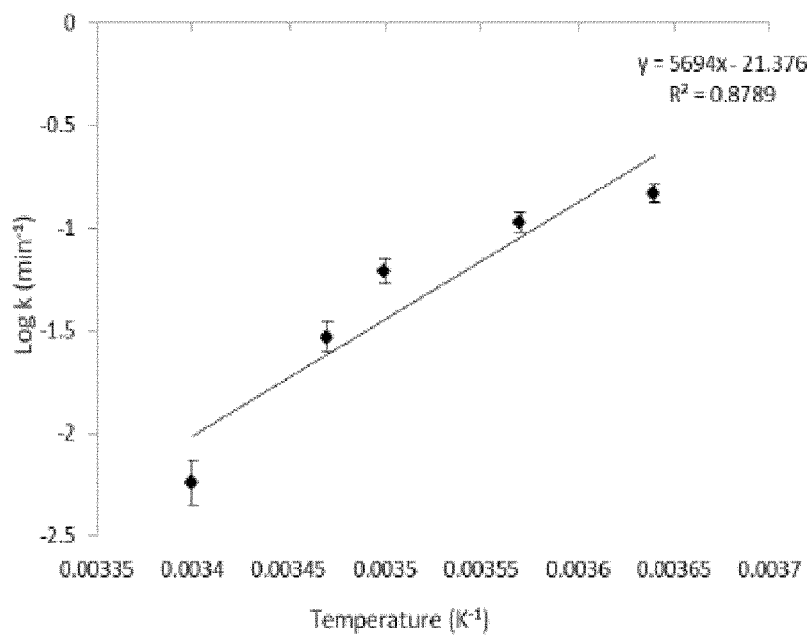
FIG. 4(A-H) are graphs showing the Arrhenius plot for cold deactivation energy (Ed) of psychrophilic enzymes in presence and absence of nanoparticles: (A) Untreated pectinase; (B) NP treated pectinase; (C) Untreated laccase; (D) NP treated laccase; (E) Untreated cellulase; (F) NP treated cellulase; (G) Untreated xylanase; (H) NP treated xylanase.
Figure 4:
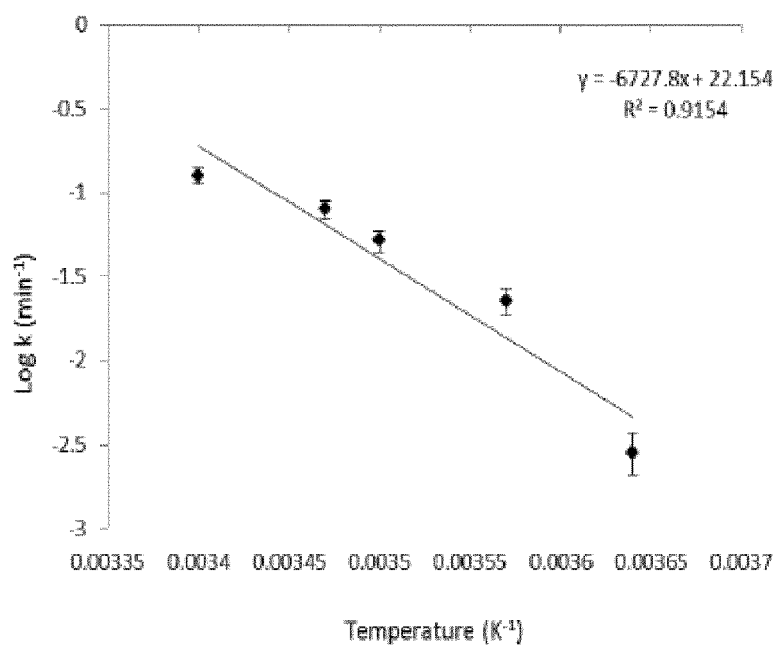
Figure 4:
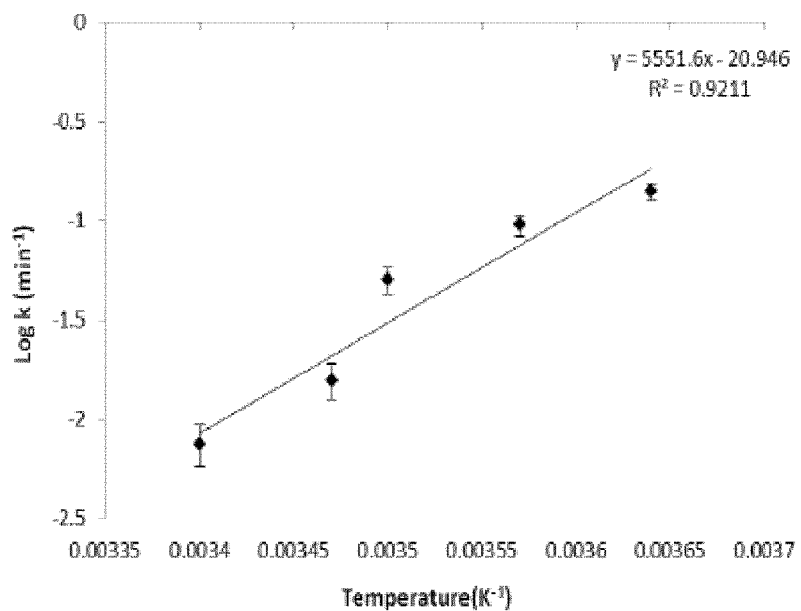
Figure 4:
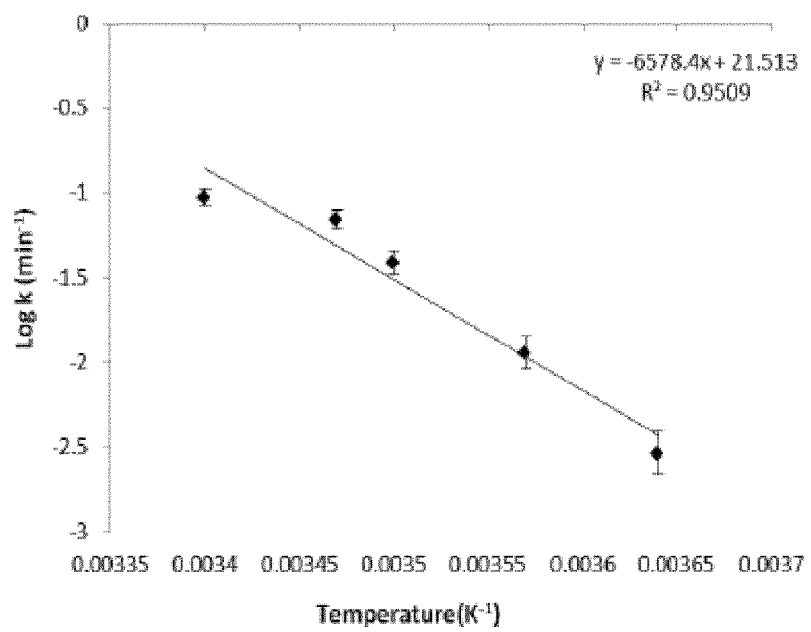
Figure 4:
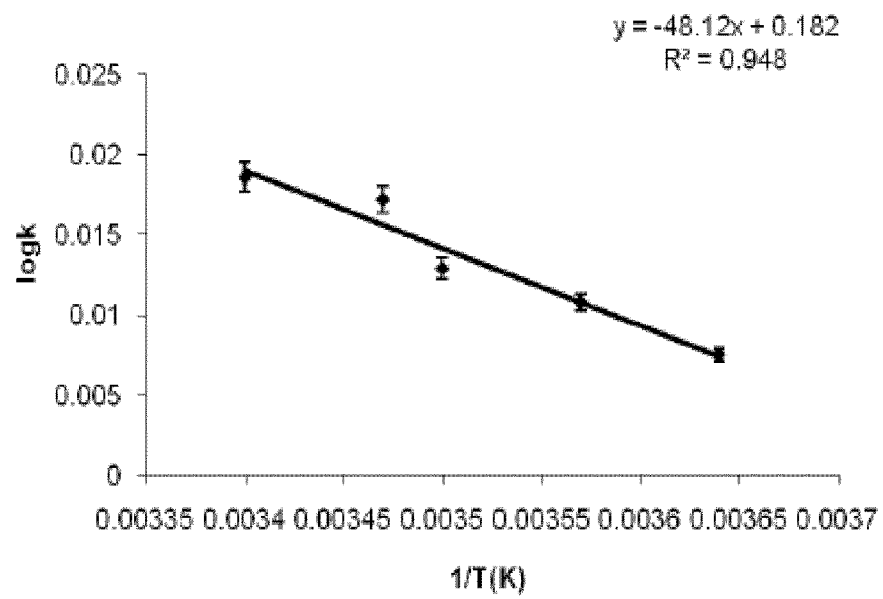
Figure 4:
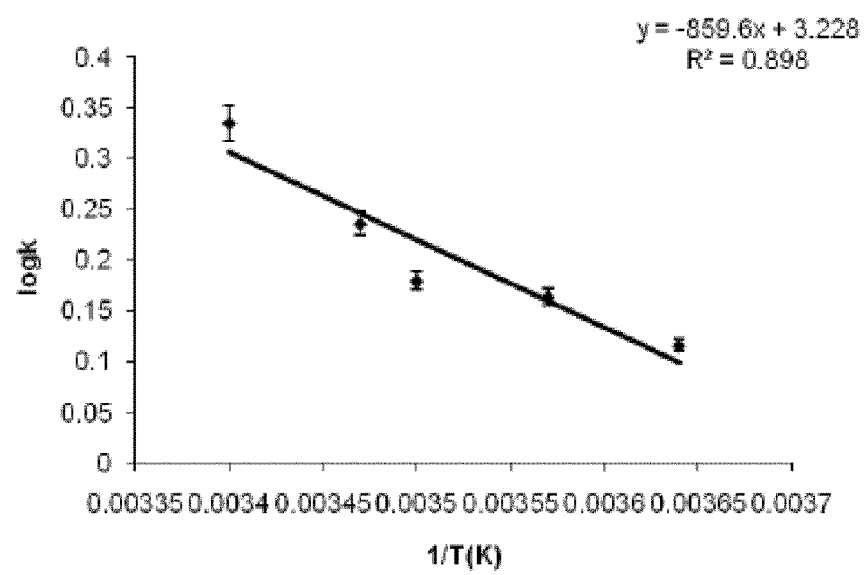
Figure 4:
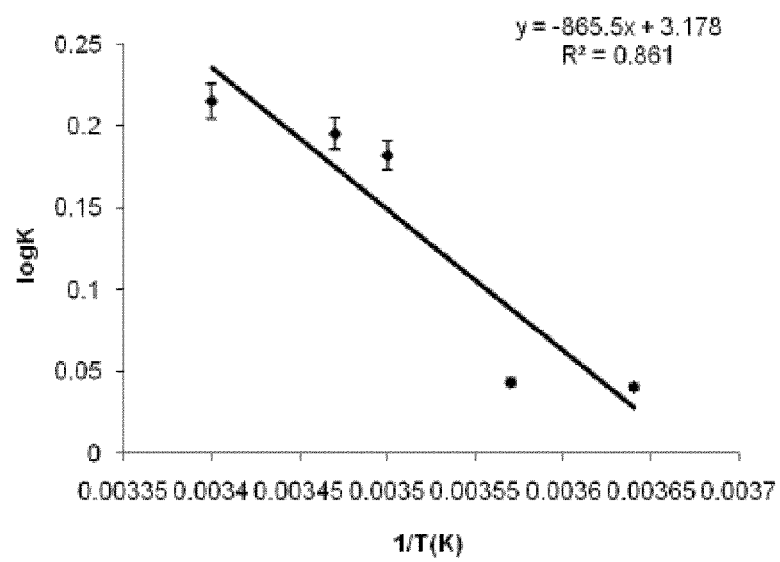
Figure 4:
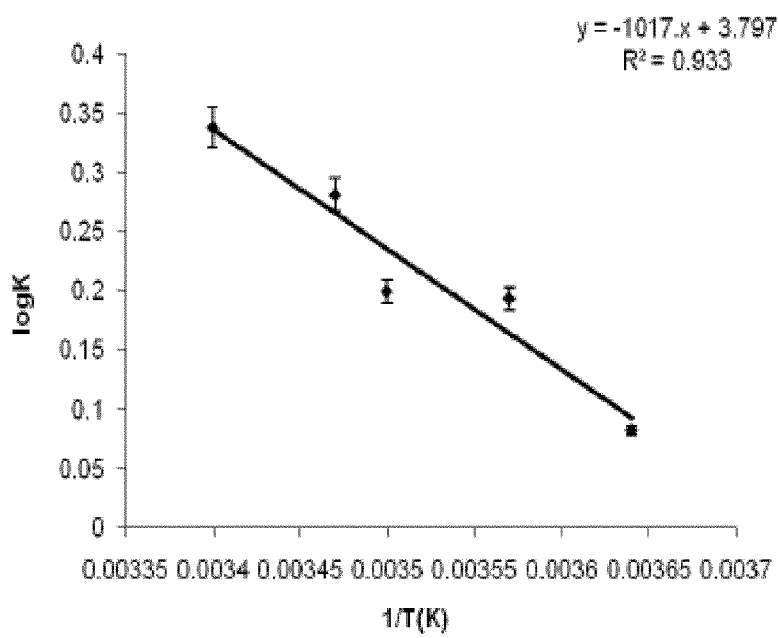

The alteration in enzyme activity with time, in the presence and absence of nanoparticles was monitored by studying time kinetics. It was observed that psychrophilic pectinase enzyme without nanoparticle treatment retained its activity for 2 hours at its optimum temperature, after which the activity decreased with time. However, nanoparticle treated enzyme retained activity for 4 hours at 4° C. FIG. 3A-B.

For example, psychrophilic laccase, in absence of NP, retained its maximum activity for 15 minutes at its optimum temperature, whereas in presence of NP, laccase retained its activity for 1 hour 15 minutes at 4° C. FIG. 3C-D.

Similarly in absence of NP, cellulase showed stability for 1.5 hours at optimum temperature, whereas in presence of NP, the retention of activity was extended to 3 hours at 4° C. FIG. 3E-F.

In case of xylanase, it was observed that in absence of NP, at optimum temperature the enzyme retained its activity for 1 hour, but in presence of NP, xylanase showed its stability for 2 hours at 4° C. FIG. 3G-H.

The experimental condition was identical as the previously described protocol. Neither $Cu^{2+}$ nor $Ca^{2+}$ ions were present in any sample because fresh milliQ water was used and no other extra supplementation of calcium or copper salt was used in the assay system.

These results show that the enzyme compositions of the present technology have enhanced psychrostability, enhance pH stability, and enhanced duration of enzyme activity as compared to a control enzyme. In particular, these results show that the enzyme compositions of the present technology are useful in processes or reactions where low temperatures and/or varied pH ranges are beneficial or required.

Example 4. Study of Psychrophilic Enzyme Stability Under Repeated Freeze Thaw Conditions The freeze thaw experiments for the psychrophilic enzymes were carried out in the presence and absence of nanoparticles to assess the alteration of stability and activity of the enzymes. Two experimental setups were used. One incorporated nanoparticle and the second setup did not incorporate nanoparticles. Enzyme activity assays were performed for both the setups with repeated cycles of freezing and thawing over a length of time until the activity was either completely lost or almost negligible.

Figure 5:
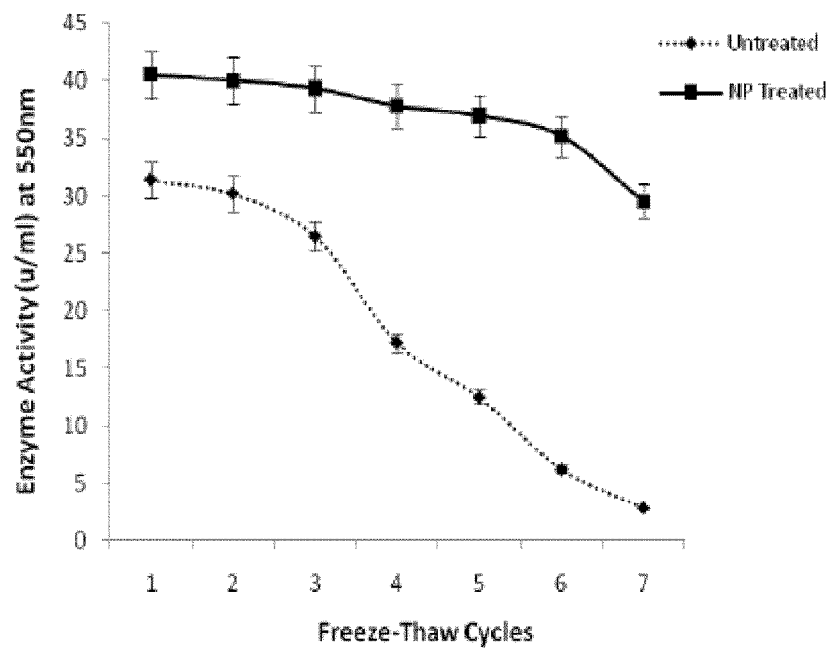
FIG. 5(A-D) are graphs comparing freeze-thaw cycles of psychrophilic enzymes in presence and absence of corresponding nanoparticles; (A) pectinase, (B) laccase, (C) cellulase and (D) xylanase.
Figure 5:
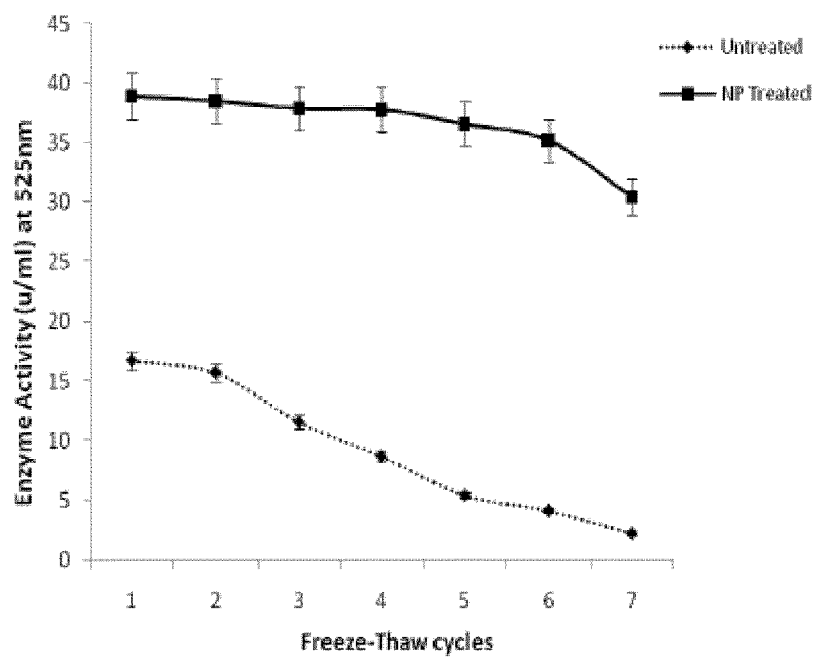
Figure 5:
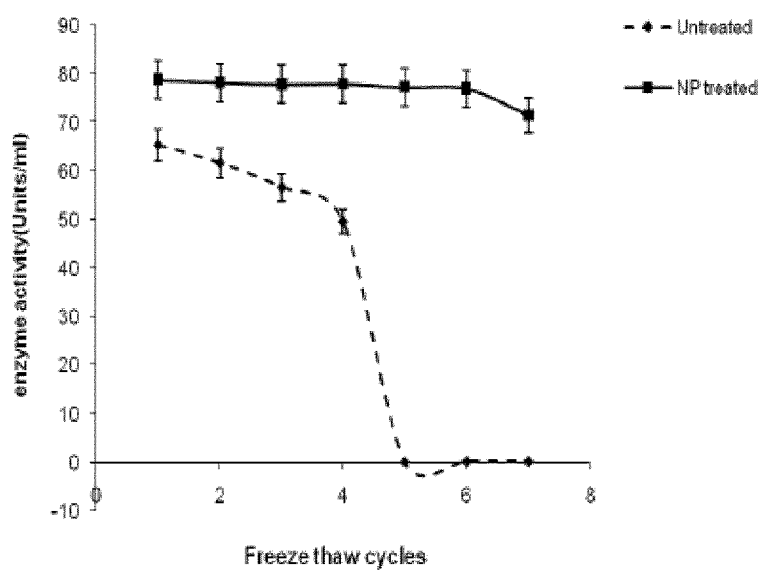
Figure 5:
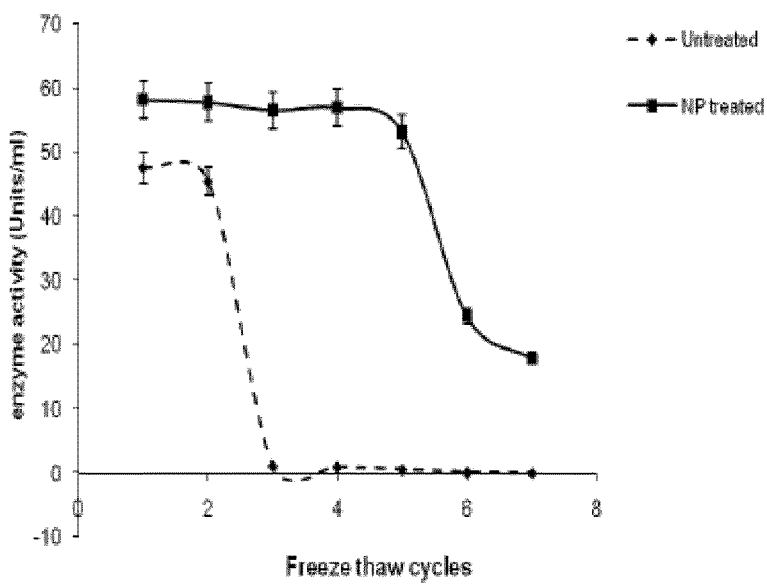

It was found that HAp NP helped partially purified psychrophilic pectinase, cellulose, and xylanase to retain their activity after several cycles of freeze-thaw cycles. In absence of NP, pectinase retained its activity for 2-3 cycles at the most, after that its activity decreased drastically. However, in the presence of NP, pectinase activity remained for 6 cycles of random freeze-thaw treatment. FIG. 5A. In case of cellulase, it was observed that, untreated cellulase retained its activity for 3-4 cycles, whereas NP treated cellulase retained its activity even after 6 consecutive cycles. FIG. 5C. Similarly, untreated xylanase retained its activity for only 2 cycles; in contrast, NP treated xylanase remained active for 5 cycles. FIG. 5D.

$Cu_2O$ NP also helped partially purified laccase to retain its activity for 7 consecutive cycles of freeze-thaw experiments, whereas untreated laccase remained active for only 2 cycles. FIG. 5B.

These results show that the enzyme compositions of the present technology maintain high enzymatic activity after many freeze-thaw cycles as compared to a control enzyme. In particular, these results show that the enzyme compositions of the present technology are useful for the storage of enzymes for repeated future use without appreciable loss of activity.

Example 5. Study of Enzyme Kinetic Parameters

The uses of enzymes in industrial processes often require reactions at low temperatures in order to improve productivity. This requires the enzymes to exhibit appropriate kinetic values at very low temperatures. The kinetic parameters (given below) were examined to gain an insight into the tolerance of the partially purified pectinase, laccase, cellulose, and xylanase to low temperature. For the study of enzyme kinetics, the buffer (25 mM Tris-HCl, pH 8.5) contained no supplementation of corresponding calcium and copper ions. Only HAp and $Cu_2O$ nanoparticle were added to the corresponding assay system (HAp NP was added to pectinase, cellulose, and xylanase assay system and $Cu_2O$ NP was added to laccase assay system).

Km, Vmax and Activation Energy (Ea)

The kinetic parameters, Km, Vmax, and the activation energy (Ea) of both HAp NP treated and untreated pectinase, cellulase and xylanase and $Cu_2O$ nanoparticle treated and untreated purified laccase enzymes were calculated. For pectinase, cellulase and xylanase, the substrate concentrations of PGA, CMC and birchwood xylan (respectively) used were from 0.015% to 1.25%. For laccase, syringaldazine substrate concentration used was from 0.2 mM to 2 mM. The incubation temperature was 4° C. for each system.

The activation energy (Ea) was calculated for the temperature range of 4-50° C. from the Arrhenius plot. The PGA, CMC, and birchwood xylan substrate concentrations for pectinase, cellulase and xylanase (respectively) were 0.75% and syringaldazin substrate concentration for laccase was 1 mM.

TABLE 2

Km, Vmax and activation energy (Ea): Nanoparticle incorporation enhances the enzyme-substrate specificity and lowers the activation energy than the untreated enzyme.

| Psychrophilic enzymes | Pectinase | | Laccase | | Cellulase | | Xylanase | |
|---|---|---|---|---|---|---|---|---|
| | Untreated | NP Treated | Untreated | NP Treated | Untreated | NP Treated | Untreated | NP Treated |
| Km | 0.45 | 0.2 | 0.589 | 0.465 | 1.25 | .11 | 5 | 0.862 |
| Vmax | 22.64 | 4.4 | 11.03 | 40 | 16.66 | 127 | 31 | 102 |
| Ea | 84.436 | 23.187 | 27.628 | 24.958 | 25.867 | 6.345 | 28.8 | 11.9 |

These results show that the enzyme compositions of the present technology have enhanced enzyme activity at low temperatures as compared to a control enzyme. In particular, these results show that the enzyme compositions of the present technology are useful in processes or reactions that require reactions at low temperatures in order to improve productivity.

Example 6. Thermal Stability of Enzyme Composition

To observe the thermal stability, $Cu_2O$ nanoparticle and NP untreated partially purified laccase samples were subjected to temperatures between 4 and 20° C. (277-293 K) for up to 10 min. Inactivation parameters comprising half-life (t1/2), decay rate constant (k) and deactivation energy (Ed) were calculated according to Ortega et al. (2004)(3). Similarly for those partially purified pectinase, cellulase and xylanase, similar protocol was followed to observe the thermal stability (for those three enzymes HAp NP was used). The PGA, CMC, and birchwood xylan substrate concentrations for pectinase, cellulase and xylanase (respectively) were 0.75% and syringaldazin substrate concentration for laccase was 1 mM.

$Cu_2O$/HAp NP supplementation increases the half-lives and lowers the decay constant of the psychrophilic enzymes with decreasing temperature. The thermal inactivation of $Cu_2O$/HAp NP treated and untreated partially purified enzymes (pectinase, laccase, cellulase and xylanase) were examined for its kinetics. A semi-logarithmic plot of residual activity versus time (between 4-20° C. or 277-293 K) for each cases were linear. FIG. 4A-H. The plots suggested that NP untreated enzymes were cold inactivated with first order kinetics, but the NP treated enzymes were cold activated with first order kinetics. The half-life (t1/2) values according to the plots were calculated (Tables 3-10). FIG. 4A-H.

TABLE 3

Psychrophilic pectinase inactivation without NP

| Pre-incubation temperature(K) | Decay constant(k) (min$^{-1}$) | Half-life(t$_{1/2}$) (min) | Ed (KJmol$^{-1}$) |
|---|---|---|---|
| 277 | 0.1475 | 4.69 | −109.023 |
| 280 | 0.107 | 6.48 | |
| 283 | 0.061 | 11.36 | |
| 288 | 0.0297 | 23.3 | |
| 293 | 0.0058 | 119.5 | |

TABLE 4

Psychrophilic pectinase inactivation with NP

| Pre-incubation temperature(K) | Decay constant(k) (min$^{-1}$) | Half-life(t$_{1/2}$) (min) | Ed (KJmol$^{-1}$) |
|---|---|---|---|
| 277 | 0.0028 | 247.5 | 128.802 |
| 280 | 0.0223 | 31.08 | |
| 283 | 0.0511 | 13.56 | |
| 288 | 0.0782 | 8.86 | |
| 293 | 0.1253 | 5.53 | |

TABLE 5

Psychrophilic Laccase inactivation without NP:

| Pre-incubation temperature(K) | Decay constant(k) (min$^{-1}$) | Half-life(t$_{1/2}$) (min) | Ed (KJmol$^{-1}$) |
|---|---|---|---|
| 277 | 0.1386 | 5.00 | −106.285 |
| 280 | 0.0934 | 7.42 | |
| 283 | 0.0499 | 13.88 | |
| 288 | 0.0154 | 45.00 | |
| 293 | 0.0074 | 93.65 | |

TABLE 6

Psychrophilic Laccase inactivation with NP:

| Pre-incubation temperature(K) | Decay constant(k) (min$^{-1}$) | Half-life(t$_{1/2}$) (min) | Ed (KJmol$^{-1}$) |
|---|---|---|---|
| 277 | 0.0029 | 238.96 | 125.95 |
| 280 | 0.0113 | 61.33 | |
| 283 | 0.0387 | 17.91 | |
| 288 | 0.0693 | 10.00 | |
| 293 | 0.0934 | 7.42 | |

TABLE 7

Psychrophilic Cellulase inactivation without NP:

| Pre-incubation temperature(K) | Decay constant(k) (min$^{-1}$) | Half-life(t$_{1/2}$) (min) | Ed (KJmol$^{-1}$) |
|---|---|---|---|
| 277 | 0.0186 | 37.26 | 0.919 |
| 280 | 0.0172 | 40.29 | |
| 283 | 0.0129 | 53.73 | |
| 288 | 0.0108 | 64.18 | |
| 293 | 0.0075 | 92.41 | |

TABLE 8

Psychrophilic Cellulase inactivation with NP:

| Pre-incubation temperature(K) | Decay constant(k) (min$^{-1}$) | Half-life(t$_{1/2}$) (min) | Ed (KJmol$^{-1}$) |
|---|---|---|---|
| 277 | 0.0062 | 111.79 | 16.447 |
| 280 | 0.0063 | 110.02 | |
| 283 | 0.0690 | 100.45 | |
| 288 | 0.01351 | 51.30 | |
| 293 | 0.01544 | 44.89 | |

TABLE 9

Psychrophilic Xylanase inactivation without NP

| Pre-incubation temperature(K) | Decay constant(k) (min$^{-1}$) | Half-life(t$_{1/2}$) (min) | Ed (KJmol$^{-1}$) |
|---|---|---|---|
| 277 | 0.2149 | 3.225 | 16.572 |
| 280 | 0.1951 | 3.552 | |
| 283 | 0.1819 | 3.810 | |
| 288 | 0.043 | 16.11 | |
| 293 | 0.040 | 17.32 | |

TABLE 10

Psychrophilic Xylanase inactivation with NP

| Pre-incubation temperature(K) | Decay constant(k) (min$^{-1}$) | Half-life(t$_{1/2}$) (min) | Ed (KJmol$^{-1}$) |
|---|---|---|---|
| 277 | 0.0099 | 70.00 | 19.487 |
| 280 | 0.0193 | 35.91 | |
| 283 | 0.0199 | 34.83 | |
| 288 | 0.0281 | 24.66 | |
| 293 | 0.0388 | 20.50 | |

These results show that the psychrophilic enzyme compositions of the present technology have enhanced enzyme activity at higher temperatures as compared to a control enzyme. In particular, these results show that the psychrophilic enzyme compositions of the present technology are useful in improving efficiency and productivity in processes or reactions that require cycling through low and high temperature. Additionally, psychrophilic enzyme compositions of the present technology provide the ability to use psychrophilic enzymes in processes or reactions that require high temperature.

Example 7. Increased Production of Total Free Amino Acids in Solution by Protease Enzyme Incorporated with Cu$_2$O Nanoparticles Corn cobs are easily available in the market and this cheap source can be readily utilized for production of reducing sugars. This study demonstrates the ability of Cu$_2$O nanoparticles to enhance protease activity by increasing free amino acid production and reducing incubation time.
Methods and Materials
Preparation of Corn Cobs
The corn cobs were de-seeded and dried completely in the oven. Thereafter, the cobs were subjected to protease treatment for enzymatic breakdown of the proteins into corresponding free amino acids. The experiment was done in presence and absence of nanoparticles. This treatment by protease was carried out to cleave the peptide bonds of the corn cobs in order to make the corn cobs content of the corn cobs more accessible to the subsequent treatment with the "enzyme mix" (which would degrade the polysaccharides and phenols).

Measurement of Protease Activity

Protease activity was assayed by azo-casein method. The enzyme source was incubated with 1% (w/v) azo-casein for 10 minutes at 37° C. in 25 mM Tris-HCl buffer of pH 8.5. The reaction was stopped by addition of 4 ml of 5% trichloroacetic acid. The contents were centrifuged at 3000×g for 10 min. One ml of the supernatant was taken and 5 ml of 0.4 M $Na_2CO_3$ was added, followed by 0.5 ml Folin-Ciocalteau reagent. The OD of samples was taken at 660 nm.

Estimation of Glucose

Amount of Glucose in the solution was estimated by using commercially available Eco-pack glucose 500 provided by ACCUREX Biomedical PVT limited. The standard and the blank samples were prepared as per instruction provided in the pack.

The test samples of glucose were prepared in presence/absence of nanoparticles and the results were read at 505 nm.

The calculation was done by the formula (provided with the pack):

O.D. of the test sample at 505 nm×100=mg % of glucose in the solution
O.D. of the standard at 505 nm Results The protease, obtained from a bacterial source was incubated with de-seeded corn cob waste for various lengths of time in presence or absence of $Cu_2O$ nanoparticle at different temperatures.

The optimal conditions that were required for production of maximal amount of total free amino acids were determined. In absence of $Cu_2O$ nanoparticles, the optimal temperature and pH for production of total free amino acids was 40° C. and 9.0, respectively. The total free amino acid produced was 31 µg/ml of the solution.

Figure 6:
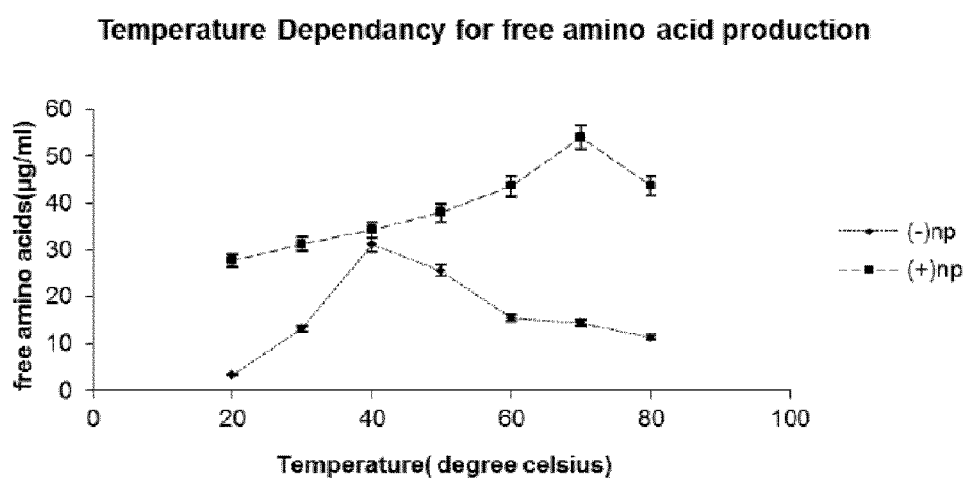
FIG. 6 is a graph comparing protease activity in the presence and absence of $Cu_2O$ NP. Additionally, the graph shows that the $Cu_2O$ NP affects the optimal temperature at which the protease is most active.
Figure 7:
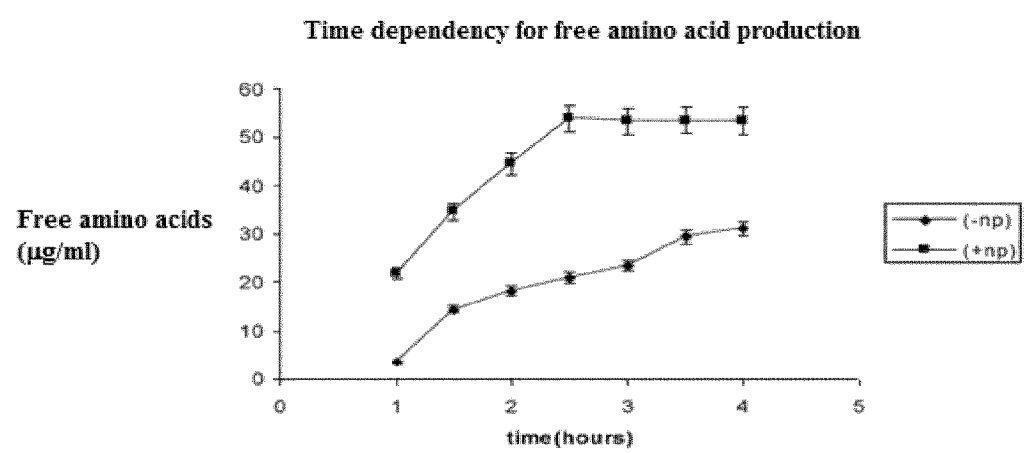
FIG. 7 is a graph illustrating the variation in production of free amino acids with time in presence and absence of $Cu_2O$ NP.
Figure 8:
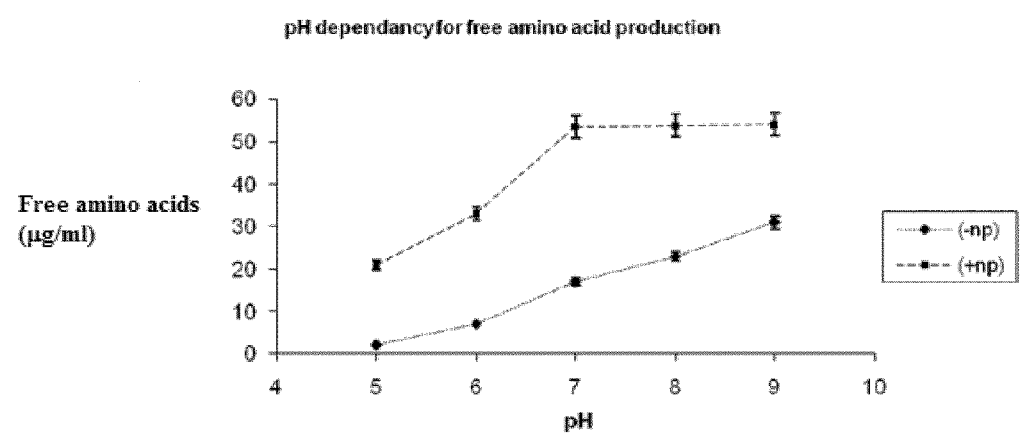
FIG. 8 is a graph illustrating the variation in production of free amino acids with pH in presence and absence of $Cu_2O$ NP.

However, the incorporation of $Cu_2O$ nanoparticles in the enzyme system, optimum production of amino acids were produced at a temperature of 70° C. FIG. 6 with an extended range of pH from 6.0-9.0. FIG. 8. The production of total free amino acids also increased to 54 µg/ml. The optimal time for production of free amino acids decreased from 4 hours to 2 hours 30 minutes FIG. 7 in presence of $Cu_2O$ nanoparticles (see Table 11).

TABLE 11

Production of Free Amino Acids

| System: (Protease + substrate) | Temperature (° C.) | Time of incubation (in hours) | pH | Amount of free amino acids produced (µg/ml) | (%) increase in presence of NP |
|---|---|---|---|---|---|
| (−) NP | 40 | 4 | 9.0 | 31 | 74 |
| (+) NP | 70 | 2.5 | 6.0-9.0 | 54 | |

This study showed that $Cu_2O$ nanoparticles enhance protease enzyme activity by extending the temperature and pH range in which the protease is active. Additionally, the $Cu_2O$ nanoparticle enhanced the protease's efficiency by reducing the time needed to produce free amino acids, while increasing the total free amino acid production.

The total free amino acids were estimated according to the method proposed by Sadasivam and Manickam (Biochemical Methods for agricultural sciences, p. 41-42 (1991)).

These results show that the mesophilic enzyme compositions of the present technology have enhanced enzyme activity at higher temperatures as compared to a control enzyme. In particular, these results show that the mesophilic enzyme compositions of the present technology are useful for increasing free amino acids from a substrate, extending the pH range for enzymatic activity, and reducing the incubation time needed to produce the free amino acids.

Example 8. Production of Glucose and Other Reducing Sugars at Low Temperatures by an Enzyme Mix from a Cell Free Extract of Psychrophilic Bacteria in the Presence of Suitable Nanoparticles The protease treated de-seeded corn cobs, from Example 7, were further subjected to incubation with an enzyme mix obtained from cell free extract of psychrophilic bacteria, in the presence of suitable nanoparticles to assess the production of reducing sugars. This enzyme mix from psychrophilic bacteria consisted of crude forms of pectate lyase, laccase, cellulase, and xylanase.

Assays were performed to measure the production of glucose and reducing sugars from dried, de-seeded protease treated corn cobs by the action of cell free extract of psychrophilic bacteria in presence and/or absence of nanoparticles. The results in Table 12 shows that nanoparticles decrease the temperature at which the enzymes remain highly active, increase the amount of reducing sugars and glucose, and decrease the incubation time required to produce the reducing sugars and glucose.

TABLE 12

Production of glucose and reducing sugars by the action of cell free extract of psychrophilic

| System: (cell free extract + corn cob) ± np | Temperature (° C.) | Time of incubation (in hours) | pH | Production in g/l | (%) increase in presences of nanoparticle |
|---|---|---|---|---|---|
| Reducing sugar(−) NP | 10.0 | 3.5 | 7.0 | 89 | 5.6 for reducing sugars |
| Reducing sugar(+) NP | 4.0 | 2.0 | 7.0-10.5 | 94 | |
| Glucose(−) NP | 10.0 | 3.5 | 7.0 | 67 | 26.86 for glucose |
| Glucose(+) NP | 4.0 | 2.0 | 7.0-10.5 | 85 | |

Figure 9:
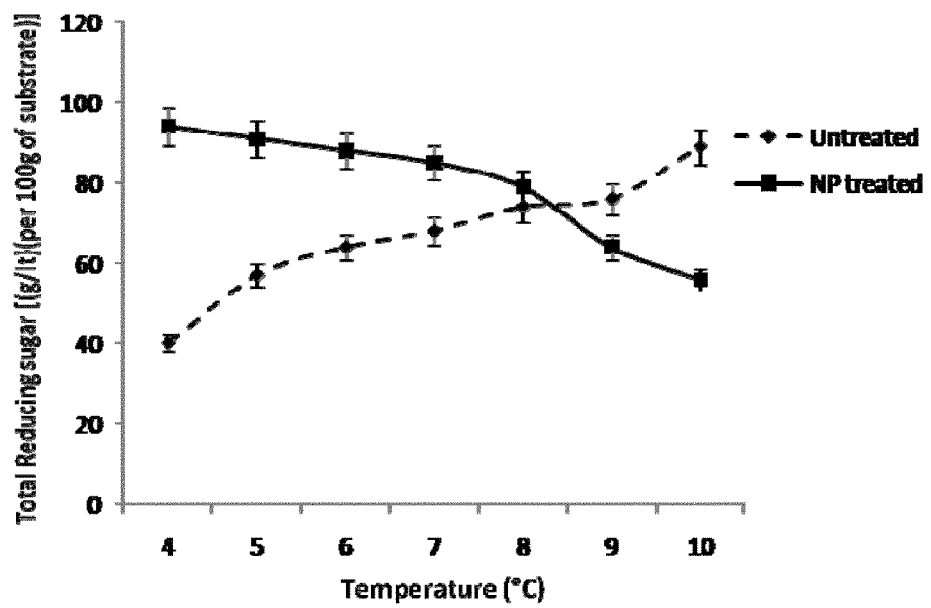
FIG. 9A is a graph showing the amount of reducing sugars produced from cell free extract at temperatures ranging from about 4° C. to about 10° C. from protease treated de-seeded corn cobs by an enzyme mix (pectate lyase, laccase, cellulase, and xylanase) either treated with or without NP.
FIG. 9B is a graph showing the amount of glucose produced from cell free extract at temperatures ranging from about 4° C. to about 10° C. from protease treated de-seeded corn cobs by an enzyme mix (pectate lyase, laccase, cellulase, and xylanase) either treated with or without NP.
Figure 9:
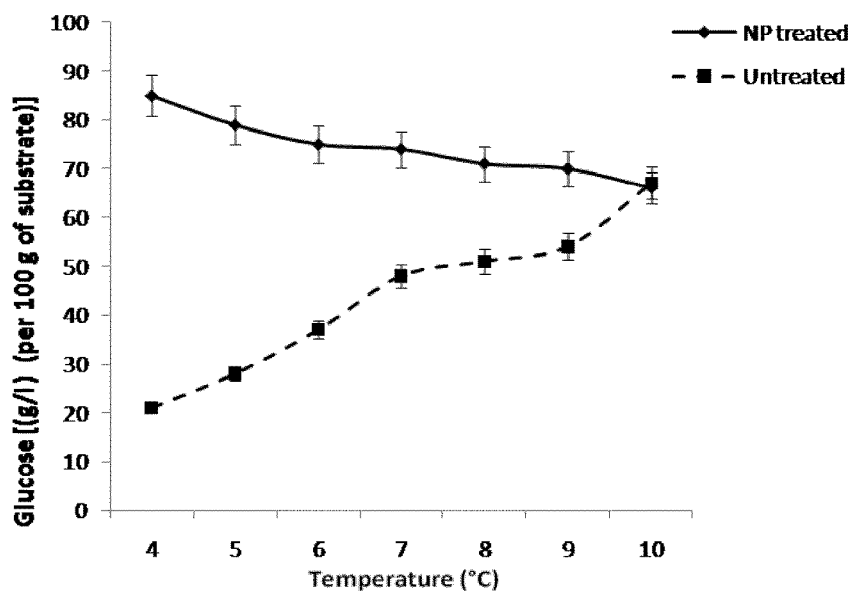
Figure 10:
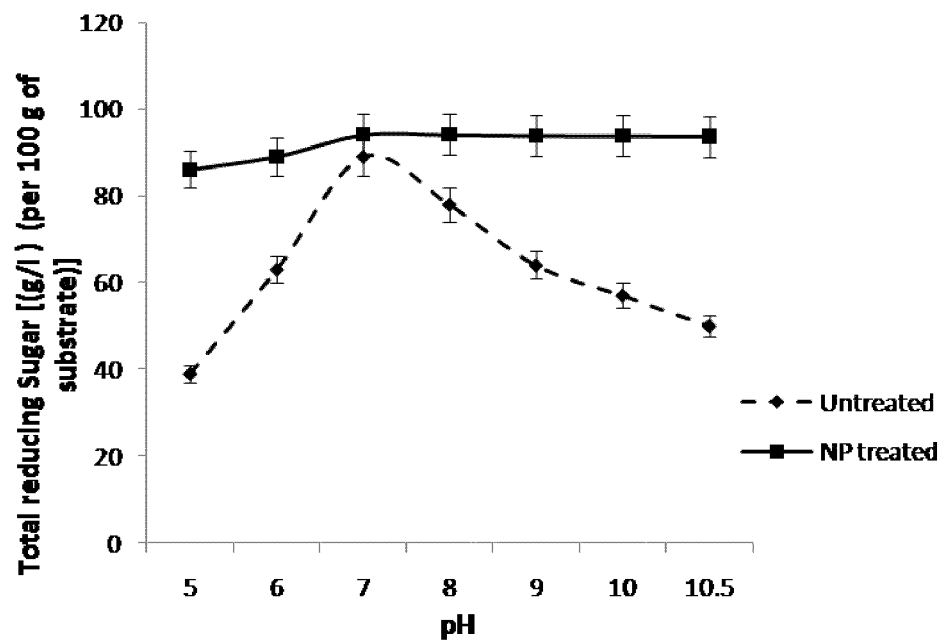
FIG. 10A is a graph showing the amount of reducing sugars produced from cell free extract at a pH range from about 5 to about 10 from protease treated de-seeded corn cobs by an enzyme mix (pectate lyase, laccase, cellulase, and xylanase) either treated with or without NP.
FIG. 10B is a graph showing the amount of glucose produced from cell free extract at a pH range from about 5 to about 10 from protease treated de-seeded corn cobs by an enzyme mix (pectate lyase, laccase, cellulase, and xylanase) either treated with or without NP.
Figure 10:
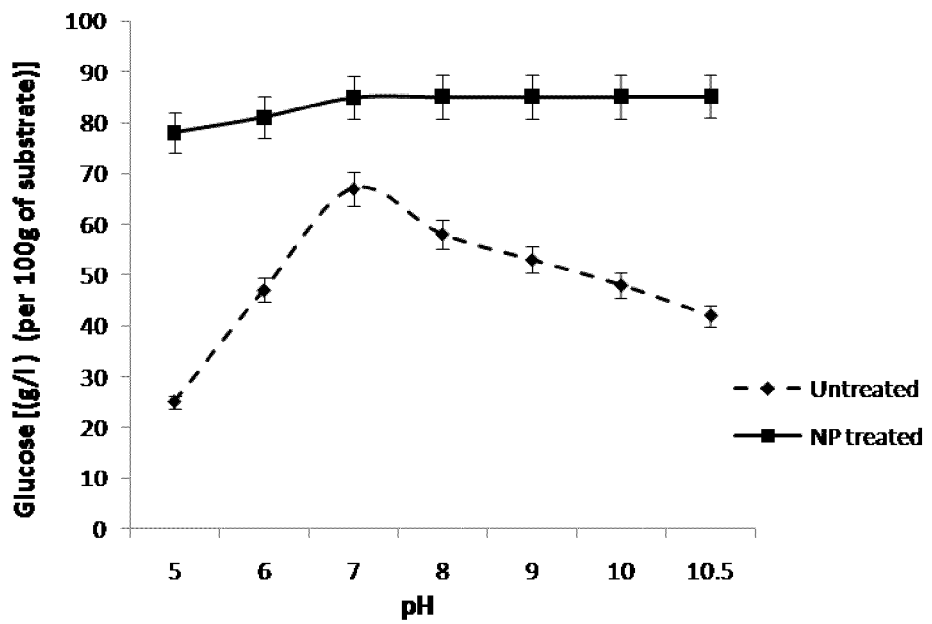

In absence of any nanoparticles, at pH 7.0 FIG. 10A and at 10° C. FIG. 9A, after 3 hours and 30 minutes of incubation, 67 g/l of glucose (per 100 g of substrate), and 89 g/l of reducing sugars (per 100 g of substrate) were produced FIG. 11A. However, upon subsequent addition of HAp nanoparticles and $Cu_2O$ nanoparticles, the optimal temperature came down from 10° C. to 4° C. FIG. 9B and there was a wider pH range, from 7.0-10.5, for enzyme activity FIG. 10B.

Figure 11:
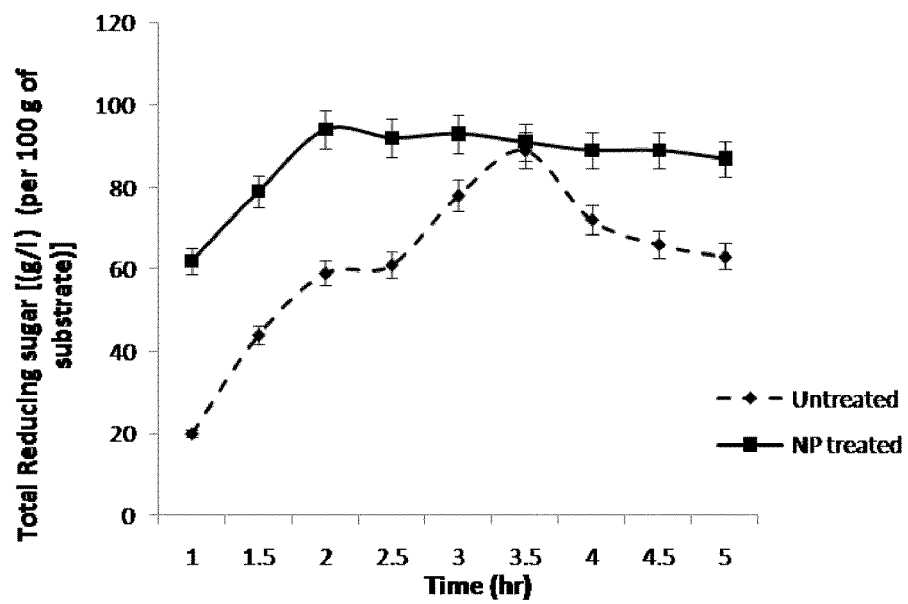
FIG. 11A is a graph showing the time dependency for reducing sugars production from cell free extract in the presence or absence of NP.
FIG. 11B is a graph showing the time dependency for glucose production from cell free extract in the presence or absence of NP.
Figure 11:
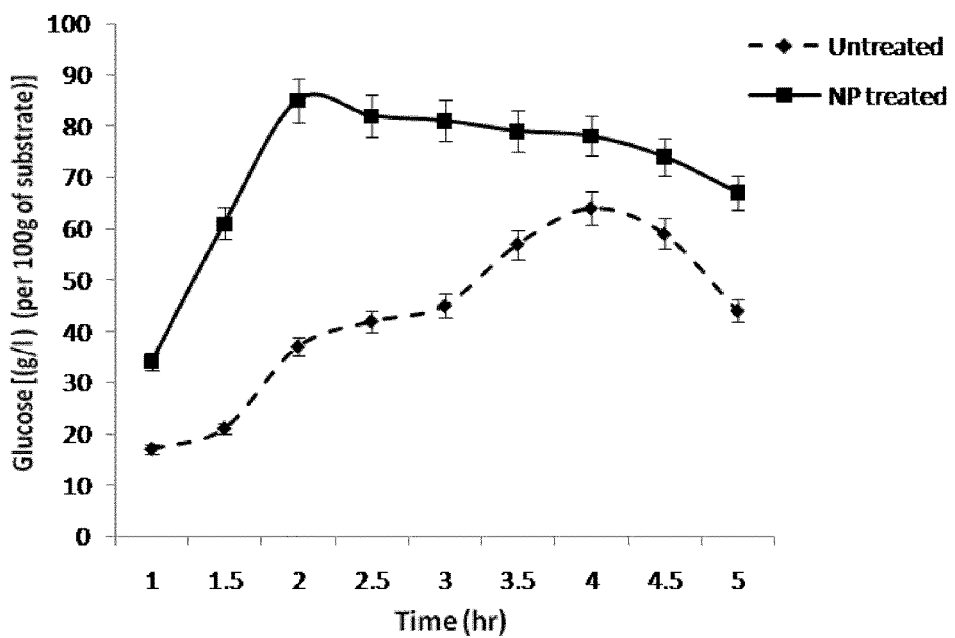

Additionally, the optimal time required for maximum production of reducing sugar was reduced to 2 hours and there was an increase in the subsequent production quantity. After 2 hours of incubation, 85 g/l of glucose (per 100 g of substrate, and 94 g/l of reducing sugars (per 100 g of substrate) were produced. FIG. 11B.

Absence of either of the nanoparticles did not bring about notable changes in the production of reducing sugars.

The experiment was repeated with normal salts of copper ($Cu_2SO_4$) and calcium ($CaCl_2$) in place of their nano-variety. However, their introduction did not influence either the rate of production of sugars or the amount of sugars produced.

These results show that the psychrophilic enzyme compositions of the present technology possess enhanced enzyme activity at lower temperatures as compared to a control enzyme. In particular, these results show that the psychrophilic enzyme compositions of the present technology are useful for increasing production of reducing sugars from a substrate, extending the pH range for enzymatic activity, and reducing the incubation time needed to produce the reducing sugars.

Example 9. Production of Industrially Important Enzymes by Live Cells of Psychrophilic Bacteria at Low Temperatures in the Presence of Suitable Nanoparticles In this study, the effects on the amount and rate of enzyme production from protease pre-treated dried and de-seeded corn cobs (See Example 7) by live psychrophilic bacteria, with or without nanoparticles was measured.

The dried and de-seeded corn cobs, after being treated with protease were incubated with live cell suspension of psychrophilic bacteria to measure the production of industrially important enzymes and to measure the production of glucose and reducing sugars.

Both of these processes were carried out in presence and absence of nanoparticles. At the time of incubation of the corn cobs with the live cell suspension, HAp nanoparticles and $Cu_2O$ nanoparticles were also introduced so as to effect if there was any change in the rate of the production of the enzymes.

Another experiment was also performed without any nanoparticles. A third experiment was performed in presence of $Cu_2SO_4$ and $CaCl_2$.

Figure 12:
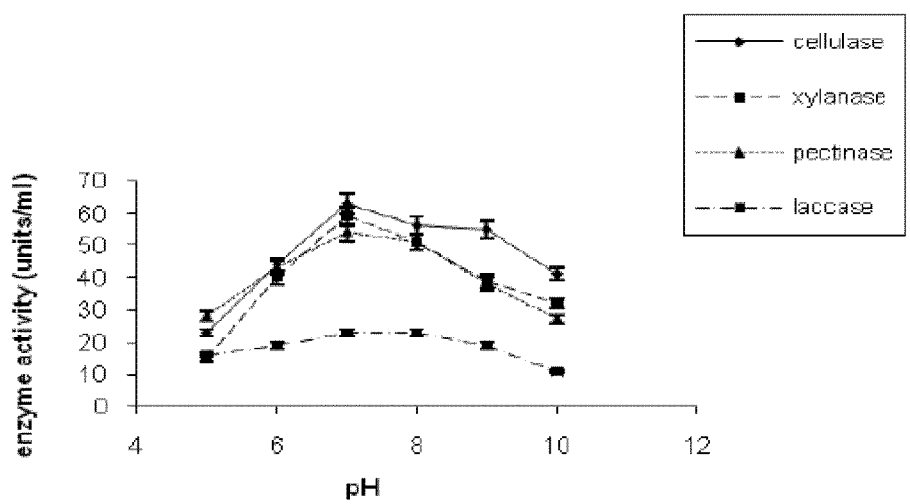
FIG. 12A is a graph showing the pH dependency of enzymes, which includes pectate lyase, laccase, cellulase, and xylanase, obtained from live cell suspensions of psychrophilic bacteria without NP.
FIG. 12B is a graph showing the pH dependency of enzymes, which includes pectate lyase, laccase, cellulase, and xylanase, obtained from live cell suspensions of psychrophilic bacteria in the presence of NP ($Cu_2O$ NP and Hap NP were added).
Figure 12:
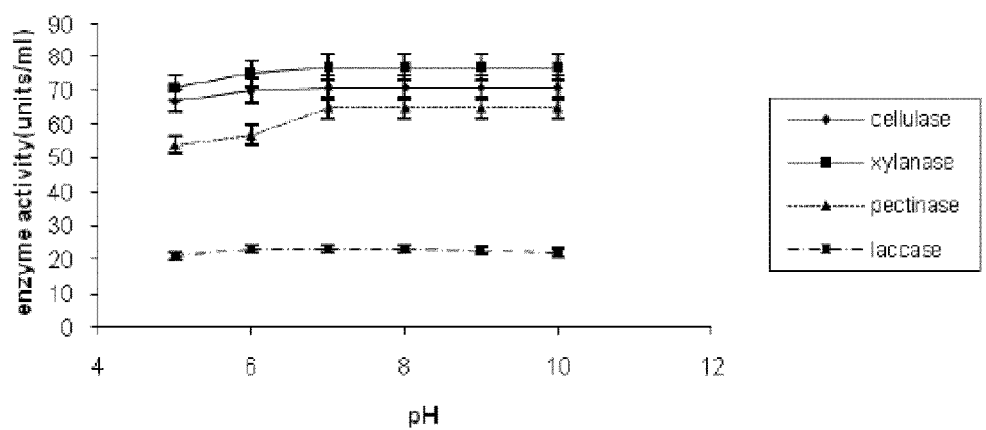
Figure 13:
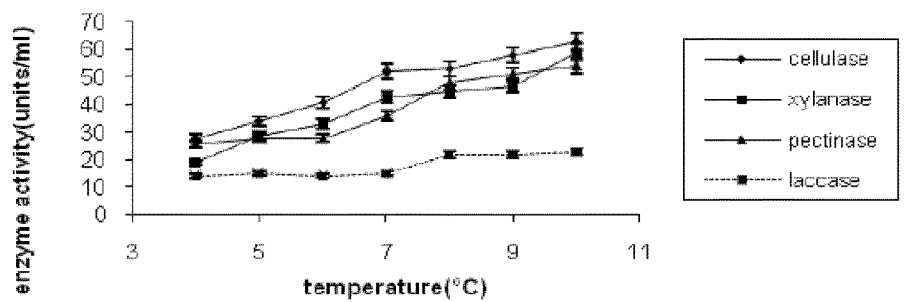
FIG. 13A is a graph showing the temperature dependency of enzymes, which includes pectate lyase, laccase, cellulase, and xylanase, obtained from live cell suspensions of psychrophilic bacteria without NP.
FIG. 13B is a graph showing the temperature dependency of enzymes, which includes pectate lyase, laccase, cellulase, and xylanase, obtained from live cell suspensions of psychrophilic bacteria in the presence of NP ($Cu_2O$ NP and Hap NP were added).
Figure 13:
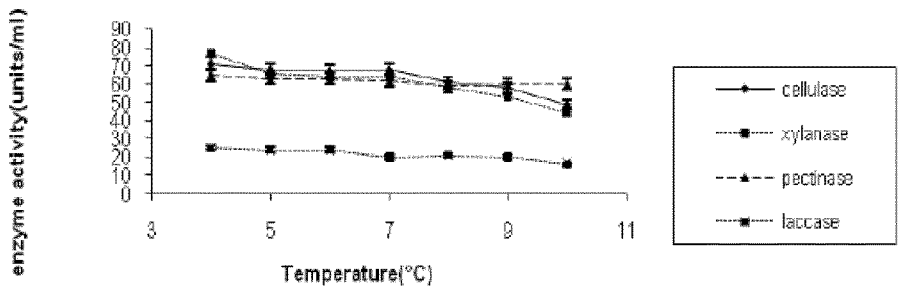
Figure 14:
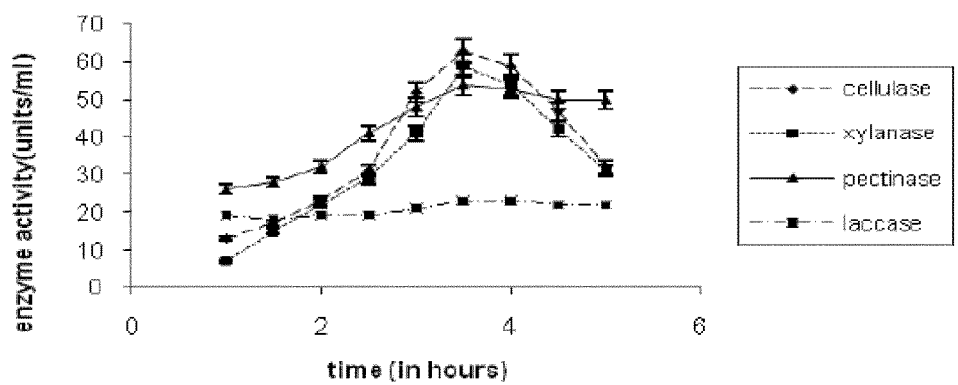
FIG. 14A is a graph showing the time dependency of enzymes, which includes pectate lyase, laccase, cellulase, and xylanase, obtained from live cell suspensions of psychrophilic bacteria without NP.
FIG. 14B is a graph showing the time dependency of enzymes, which includes pectate lyase, laccase, cellulase, and xylanase, obtained from live cell suspensions of psychrophilic bacteria in the presence of NP ($Cu_2O$ NP and Hap NP were added).
Figure 14:
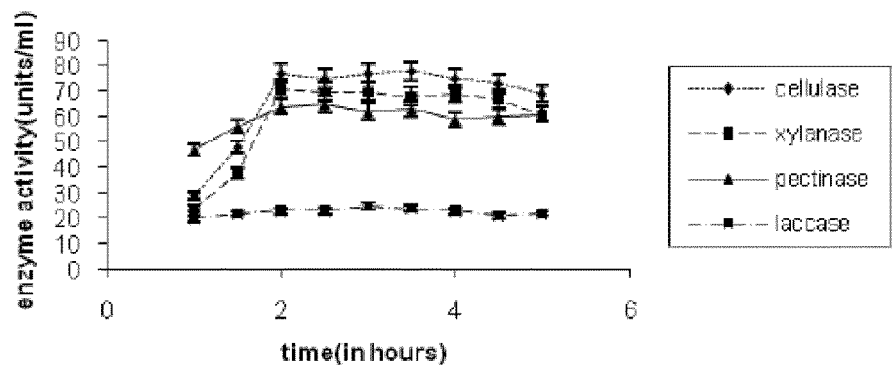

In absence of any nanoparticles, at pH 7.0 FIG. 12A, and at 10° C. FIG. 13A, after 3 hours and 30 minutes of incubation, 63 units/ml of cellulase (per 100 g of substrate), 59 units/ml of xylanase (per 100 g of substrate), 54 units/ml of pectate lyase (per 100 g of substrate) and 23 units/ml of laccase (per 100 g of substrate) were produced. FIG. 14A.

However, upon subsequent addition of HAp nanoparticles and $Cu_2O$ nanoparticles, the optimal temperature for enzyme production came down from 10° C. to 4° C. FIG. 13B and the pH range for enzyme production increased from 7.0-10.5. FIG. 12B.

Additionally, in the presence of HAp nanoparticles and $Cu_2O$ nanoparticles, the time to achieve maximum production of cellulase and xylanase was observed after 2 hours of incubation. FIG. 14B. The amounts of cellulase and xylanase produced were measured at 71 units/ml of cellulase (per 100 g of substrate) and 77 units/ml of xylanase (per 100 g of substrate). FIG. 14B. The time to achieve maximum production of pectate lyase activity was observed after 2.5 hours of incubation, and 65 units/ml of pectate lyase (per 100 g of substrate) was produced. FIG. 14B. The time to achieve maximum production of laccase was found after 3 hours of incubation with 25 units/ml of laccase (per 100 g of substrate) produced (Table 13).

TABLE 13

Production of enzymes from dried, de-seeded protease treated corn cobs by live cell suspensions of psychrophilic bacteria in the presence or absence of nanoparticles

| System: (live cell suspension + corn cob) ± np | Temperature (° C.) | Time of incubation (in hours) | pH | Production in g/ml. | (%) increase in presences of nanoparticle |
|---|---|---|---|---|---|
| Pectate-lyase(−) NP | 10 | 3.5 | 7.0 | 54 | 20.37 (for pectate lyase) |
| Pectate-lyase(+) NP | 4 | 2.5 | 7.0-10.5 | 65 | |
| Laccase (−) NP | 10 | 3.5 | 7.0 | 23 | 8.695 (for laccase) |
| Laccase (+) NP | 4 | 3.0 | 7.0-10.5 | 25 | |
| Cellulase (−) NP | 10 | 3.5 | 7.0 | 63 | 12.69 (for cellulase) |
| Cellulase (+) NP | 4 | 2.0 | 7.0-10.5 | 71 | |
| Xylanase (−) NP | 10 | 3.5 | 7.0 | 59 | 30.50(for xylanase) |
| Xylanase (+) NP | 4 | 2.0 | 7.0-10.5 | 77 | |

These results show that live cell compositions of the present technology that have cells from psychrophilic bacteria also have enhanced enzyme activity at lower temperatures as compared to a control enzyme. In particular, these results show that the psychrophilic live cells compositions of the present technology are useful for increasing production of reducing sugars from a substrate, extending the pH range for enzymatic activity, and reducing the incubation time needed to produce the reducing sugars.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What is claimed:
1. A composition comprising:
   at least one nanoparticle, wherein the nanoparticle comprises one or more of a cuprous oxide, a hydroxyapatite, magnesium chloride, manganese chloride, calcium chloride, zinc, magnesium, manganese, or a combination thereof; and
   at least one psychrophilic enzyme in contact with the nanoparticle, but not linked to the nanoparticle, and wherein the composition has an enhanced activity compared to a control psychrophilic enzyme.

2. The composition of claim 1, wherein the psychrophilic enzyme comprises one or more of laccase, pectinase, cellulase, xylanase, or a combination thereof.

3. The composition of claim 1, wherein the psychrophilic enzyme comprises a recombinant enzyme.

4. The composition of claim 1, wherein the psychrophilic enzyme in contact with the nanoparticle facilitates an enhanced activity at a temperature of about 2° C. to about 10° C. as compared to the control psychrophilic enzyme.

5. The composition of claim 1, wherein the composition has an enhanced activity at a pH between about 2 to 6 and between about 8 to 11 as compared to the control psychrophilic enzyme.

6. The composition of claim 1, wherein the ratio of nanoparticles to psychrophilic enzymes (wt/wt) is between about 1:4 to about 1:1.

7. A method of making an enzyme composition, the method comprising:
contacting at least one nanoparticle wherein the nanoparticle comprises one or more of a cuprous oxide, a hydroxyapatite, magnesium chloride, manganese chloride, calcium chloride, zinc, magnesium, manganese, or a combination thereof and at least one psychrophilic enzyme, wherein the psychrophilic enzyme is in contact with the nanoparticle, but not linked to the nanoparticle, and wherein the composition has an enhanced activity compared to a control psychrophilic enzyme.

8. The method of claim 7, wherein contacting at least one nanoparticle comprises contacting one or more nanoparticles of cuprous oxide, hydroxyapatite, magnesium chloride, manganese chloride, calcium chloride, zinc, magnesium, manganese, or a combination thereof.

9. The method of claim 7, wherein contacting at least one psychrophilic enzyme comprises contacting one or more of laccase, pectinase, cellulase, xylanase, or a combination thereof.

10. The method of claim 7, wherein the psychrophilic enzyme comprises a recombinant enzyme.

11. A method of treating a material, the method comprising:
contacting the material with a composition, wherein the composition comprises:
at least one nanoparticle, wherein the nanoparticle comprises one or more of a cuprous oxide, a hydroxyapatite, magnesium chloride, manganese chloride, calcium chloride, zinc, magnesium, manganese, or a combination thereof; and
at least one psychrophilic enzyme in contact with the nanoparticle, but not linked to the nanoparticle, and wherein the composition has enhanced activity compared to a control psychrophilic enzyme.

12. The method of claim 11, wherein the contacting is carried out at a temperature of about 2° C. to about 10° C.

13. The method of claim 11, wherein the contacting is carried out at a pH between about 2 to 6 and between about 8-11.

14. The method of claim 11, wherein the contacting is performed for a time period of at least about 1 hour, at least about 2 hours, at least about 3 hours, at least about 4 hours, or at least about 6 hours.

15. The method of claim 11, wherein contacting the material with the composition comprises contacting a mixture comprising de-seeded corncobs and/or de-seeded corncob waste and a protease composition with the composition.

16. The method of claim 11, wherein contacting the material with the composition comprises contacting the material with the composition that comprises nanoparticles selected from cuprous oxide, hydroxyapatite, magnesium chloride, manganese chloride, calcium chloride, zinc, magnesium, manganese, or a combination thereof.

17. The method of claim 11, wherein contacting the material with the composition comprises contacting the material with the composition that comprises psychrophilic enzymes selected from laccase, pectate lyase, cellulase, xylanase, and combinations thereof.

18. The method of claim 15, wherein the proteases composition comprises bacterial proteases.

19. The method of claim 11, wherein the ratio of nanoparticles to psychrophilic enzyme (wt/wt) in the composition is between about 1:4 to about 1:1.

20. The method of claim 15, further comprising:
forming the mixture by contacting the de-seeded corncobs and/or de-seeded corncob waste and the protease composition in the presence of cuprous oxide nanoparticles;
incubating the mixture at about 45° C. to about 90° C. to create a plurality of free amino acids; and
producing reducing sugars and glucose.

21. The method of claim 20, wherein incubating the mixture is carried out for a time period about 1 to about 3 hours.

22. The method of claim 20, wherein the ratio of cuprous oxide nanoparticles to the protease is about 1:3.

23. The composition of claim 1, wherein the psychrophilic enzyme is extracted from bacteria.

* * * * *

UNITED STATES PATENT AND TRADEMARK OFFICE
CERTIFICATE OF CORRECTION

PATENT NO. : 9,790,529 B2
APPLICATION NO. : 14/455699
DATED : October 17, 2017
INVENTOR(S) : Chakraborty et al.

It is certified that error appears in the above-identified patent and that said Letters Patent is hereby corrected as shown below:

On the Title Page

In Item (71), under "Applicant", in Column 1, Lines 1-2, delete "University of Calcutta, Kolkataa, West Bengal (IN)" and insert -- University of Calcutta, Kolkata, West Bengal (IN) --, therefor.

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*